United States Patent
Käslin et al.

(12) 
(10) Patent No.: US 6,632,978 B1
(45) Date of Patent: Oct. 14, 2003

(54) TRANSGENIC ANIMALS FOR STUDYING REGULATION OF GENES

(75) Inventors: Edgar Käslin, Basel (CH); Marcel Luyten, Arisdorf (CH); Hans-Günter Zerwes, Lörrach (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/693,011

(22) Filed: Oct. 20, 2000

(30) Foreign Application Priority Data

Oct. 22, 1999 (GB) .............................................. 9925125

(51) Int. Cl.7 ............................................ A01K 67/027
(52) U.S. Cl. ....................................................... 800/18
(58) Field of Search ................................ 800/18, 3, 22; 435/183

(56) References Cited

U.S. PATENT DOCUMENTS 5,151,508 A        9/1992   Salbaum et al. ............... 536/27
6,217,847 B1 *    4/2001   Contag et al. ................ 424/9.1

FOREIGN PATENT DOCUMENTS

WO        WO 99/43783         9/1999

OTHER PUBLICATIONS

Yang et al., Quantification of gene expression with a secreted alkaline phosphatase reporter system, 1997, Biotechniques, vol. 23, pp. 1110–1114.*

Campbell et al., Totipotency or multipotentiality of cultured cells: Applications and Progress, 1997, Theriogenology, vol. 47, pp. 63–72.*

Bradley et al., Modifying the mouse: design and desire, 1992, Bio/Technology, vol. 10, pp. 534–539.*

Sigmund, Viewpoint: Are studies in genetically altered mice out of control?, 2000, Arterioscler Thromb. Vasc. Biol., vol. 20, pp. 1425–1429.*

Wall, Transgenic livestock: Progress and prospects for the future, 1996, Theriogenology, vol. 45, pp. 57–68.*

Carlsen et al., Keystone Symposium, NF–κB Regulation and Function: From Basic Research to Drug Development, Tahoe City Feb. 22–27, Abstract 205 (2000).

Zerwes et al., Keystone Symposium, NFκB Regulation and Function: From Basic Research to Drug Development, Tahoe City Feb. 22–27, Abstract 261 and Poster (2000).

Ray K.P. et al., Biochem. J., vol. 328, pp. 707–715 (1997).

Gupta M.P. et al., Molecular and Cellular Biochemistry, vol. 157, pp. 117–124 (1996).

Ogg, M.S. et al., Xenobiotica, vol. 29, No. 3, pp. 269–279 (1999).

* cited by examiner

*Primary Examiner*—Anne-Marie Falk
*Assistant Examiner*—Celine Qian
(74) *Attorney, Agent, or Firm*—Thomas R. Savitsky

(57) ABSTRACT

A transgenic non-human animal (e.g., a transgenic mouse) comprising a polynucleotide encoding a soluble marker protein functionally linked to a regulatory sequence of an endogenous gene encoding E-selectin. Also described are methods for detecting modulators of the E-selectin gene using said transgenic non-human animal, and cultured cells obtained therefrom.

1 Claim, 8 Drawing Sheets

Figure 2
(a) Endogenous E-selectin locus.
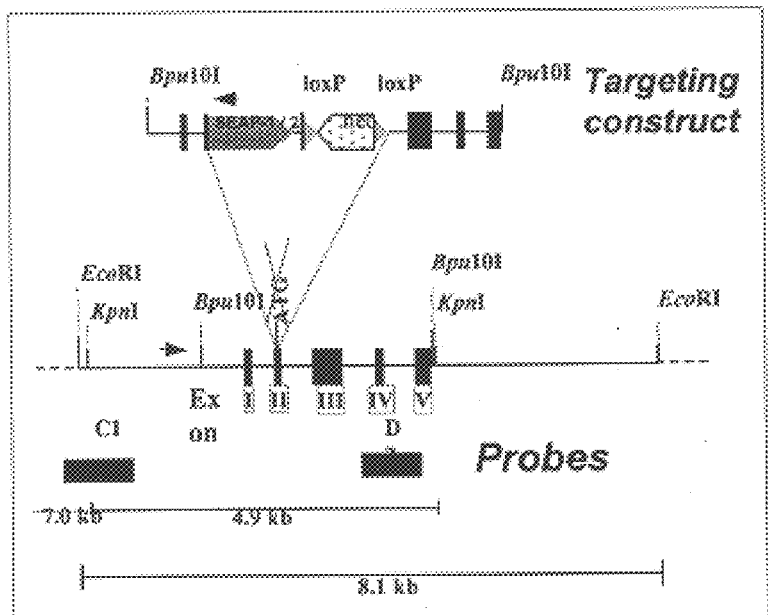
(b) Targeted locus.
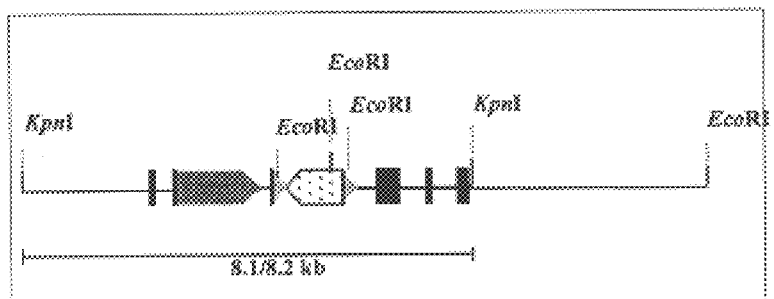
(c) Targeted locus after Cre-mediated neo cassette removal.
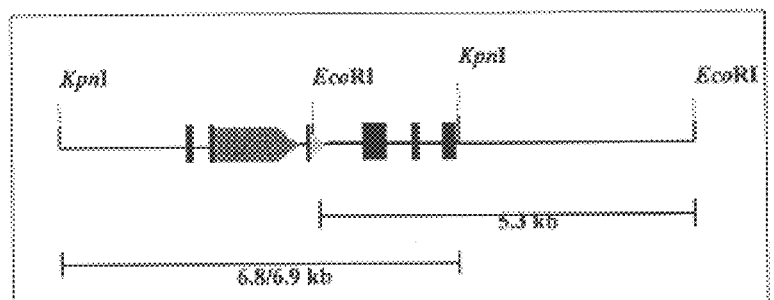

Induction of SEAP by cytokines or LPS.

Analysis of SEAP expression in the two lines.

Comparison of heterozygous and homozygous animals.

Figure 6
Alkaline phosphatase histochemistry.
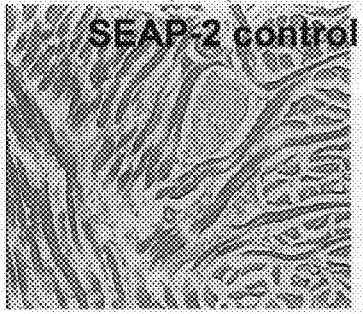
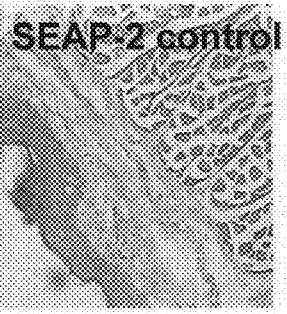
E-selectin immunostain.
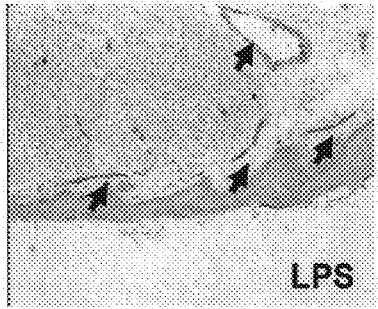
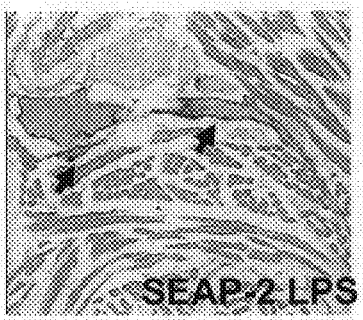
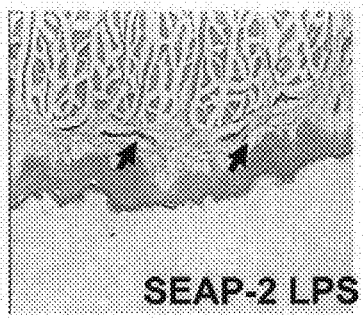
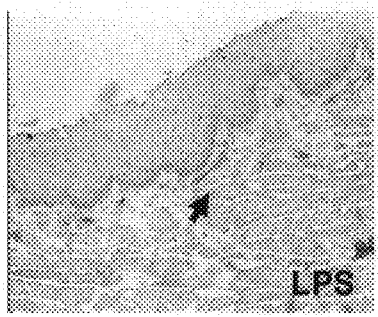

Inhibition of SEAP expression by proteasome inhibitor.

SEQUENCE LISTING

```
<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: PRIMER

<400> SEQUENCE: 1
gcagtgctca gtggtcctcg a                                             21

<210> SEQ ID NO 2
<211> LENGTH: 27
<212> TYPE: DNA
<213> ORGANISM: Artificial Sequence
<220> FEATURE:
<223> OTHER INFORMATION: PRIMER

<400> SEQUENCE: 2
tcaattgact ccagcagttg ctttcat                                       27

<210> SEQ ID NO 3
<211> LENGTH: 42
<212> TYPE: DNA
<213> ORGANISM: Artificial Sequence
<220> FEATURE:
<223> OTHER INFORMATION: PRIMER

<400> SEQUENCE: 3
gaaagcaact gctggagtca attgaatgcc tcgcgctttc tc                      42

<210> SEQ ID NO 4
<211> LENGTH: 21
<212> TYPE: DNA
<213> ORGANISM: Artificial Sequence
<220> FEATURE:
<223> OTHER INFORMATION: PRIMER

<400> SEQUENCE: 4
gctaatcacc ataacgca c                                               21

<210> SEQ ID NO 5
<211> LENGTH: 28
<212> TYPE: DNA
<213> ORGANISM: Artificial Sequence
<220> FEATURE:
<223> OTHER INFORMATION: PRIMER

<400> SEQUENCE: 5
cctttccaac ttgcttcctt tatctgag                                      28

<210> SEQ ID NO 6
<211> LENGTH: 26
```

-continued

```
<212> TYPE: DNA
<213> ORGANISM: Artificial Sequence
<220> FEATURE:
<223> OTHER INFORMATION: PRIMER

<400> SEQUENCE: 6
agtttgtcct tcttctgccc ttttag                                        26

<210> SEQ ID NO 7
<211> LENGTH: 18
<212> TYPE: DNA
<213> ORGANISM: Artificial Sequence
<220> FEATURE:
<223> OTHER INFORMATION: PRIMER

<400> SEQUENCE: 7
cctctccccg tggcatcc                                                 18

<210> SEQ ID NO 8
<211> LENGTH: 22
<212> TYPE: DNA
<213> ORGANISM: Artificial Sequence
<220> FEATURE:
<223> OTHER INFORMATION: PRIMER

<400> SEQUENCE: 8
aagtccgggt tctcctcctc aa                                            22

<210> SEQ ID NO 9
<211> LENGTH: 6408
<212> TYPE: DNA
<213> ORGANISM: Artificial Sequence
<220> FEATURE:
<223> OTHER INFORMATION: TARGETING SEQUENCE

<400> SEQUENCE: 9
cgataagctt gatttagcat ataatcagcg gtctaggtca ctaagtaggt actgtgtcac     60
tacagatacc atattaccac tgttgaaacg agaaatctag tatgaataga acatgagaag    120
aaacattcag gaatgactcc cctgcacccc agtgcctgtt aggatggcct aagtagcag     180 tgactgagca gaaccttggc actgatgtac gtatcatcaa cagttatcca caagaaaatc    240
gagagtgaca gatcatgggt aataaaatac tcttagtttg ctcatctttg tgaaaccaag    300
ttctacactt gattgataat ggtaattaga ctttataaca caagacttaa catcacacac    360
ttgtatccca tttgataaaa ctgcatacaa atataagagc ccagaaaaag aattaattta    420
gaggggcaga gtctctgaca tcactatgaa agtgttttaa ctcagtggat attcccagaa    480
aactttttgg atgcagttga gaatttcctc ttagccagat tttgataata atgtcctatg    540
actcacagga agccagctcc cctataaaga ggctccagca gaagcagtgc tcagtggtcc    600
tcgactgact acacagcaaa actgcgagaa gaacggatag agagaagcag gagcaataca    660
cctaagggat ccaacgccag aacaacaatt ccactgaaca gtaagtgcgg attccgaacc    720
agaggagcct tgggcccgaa gcatagattt atgtgtgctc acatacgcaa aaaaaaaaa    780 aaaaagtcat tctgattaaa aaagacctgt ctaaactgtt atagtgttgt aattaatacc    840
tacattttct ctttgtttaa aatgatggaa atcttaaagt ctgcatttat tctccatgct    900
agatgcctgt gaaataaggg atgaggtaca ggattctaaa acctcacagc tttgacttaa    960
atgctgttgt agaaggatgt gagtaacccg cacttagaat ttccttctgt gactaattct   1020
gcactttctc tcctcaggaa agtttctcca gtctagcgcc tggatgaaag caactgctgg   1080
```

-continued

| | |
|---|---|
| agtcaattcg cccaccatgc tgctgctgct gctgctgctg ggcctgaggc tacagctctc | 1140 |
| cctgggcatc atcccagttg aggaggagaa cccggacttc tggaaccgcg aggcagccga | 1200 |
| ggccctgggt gccgccaaga agctgcagcc tgcacagaca gccgccaaga acctcatcat | 1260 |
| cttcctgggc gatgggatgg gggtgtctac ggtgacagct gccaggatcc taaaagggca | 1320 |
| gaagaaggac aaactggggc tgagatacc cctggccatg accgcttcc catatgtggc | 1380 |
| tctgtccaag acatacaatg tagacaaaca tgtgccagac agtggagcca cagccacggc | 1440 |
| ctacctgtgc ggggtcaagg caacttcca gaccattggc ttgagtgcag ccgcccgctt | 1500 |
| taaccagtgc aacacgacac gcggcaacga ggtcatctcc gtgatgaatc gggccaagaa | 1560 |
| agcagggaag tcagtgggag tggtaaccac cacacgagtg cagcacgcct cgccagccgg | 1620 |
| cacctacgcc cacacggtga accgcaactg gtactcggac gccgacgtgc ctgcctcggc | 1680 |
| ccgccaggag gggtgccagg acatcgctac gcagctcatc tccaacatgg acattgacgt | 1740 |
| gatcctaggt ggaggccgaa agtacatgtt tcgcatggga acccagacc ctgagtaccc | 1800 |
| agatgactac agccaaggtg ggaccaggct ggacgggaag aatctggtgc aggaatggct | 1860 |
| ggcgaagcgc cagggtgccc ggtatgtgtg gaaccgcact gagctcatgc aggcttccct | 1920 |
| ggacccgtct gtgacccatc tcatgggtct ctttgagcct ggagacatga atacgagat | 1980 |
| ccaccgagac tccacactgg accctcct gatggagatg acagaggctg ccctgcgcct | 2040 |
| gctgagcagg aaccccgcg gcttcttcct cttcgtggag ggtggtcgca tcgaccatgg | 2100 |
| tcatcatgaa gcagggcttt accgggcact gactgagacg atcatgttcg acgacgccat | 2160 |
| tgagagggcg ggccagctca ccagcgagga ggacacgctg agcctcgtca ctgccgacca | 2220 |
| ctcccacgtc ttctccttcg gaggctaccc cctgcgaggg agctccatct cgggctggc | 2280 |
| ccctggcaag gcccgggaca ggaaggccta cacggtcctc ctatacggaa acggtccagg | 2340 |
| ctatgtgctc aaggacggcg cccggccgga tgttaccgag agcgagagcg ggagccccga | 2400 |
| gtatcggcag cagtcagcag tgcccctgga cgaagagacc cacgcaggcg aggacgtggc | 2460 |
| ggtgttcgcg cgcggcccgc aggcgcacct ggttcacggc gtgcaggagc agaccttcat | 2520 |
| agcgcacgtc atggccttcg ccgcctgcct ggagccctac accgcctgcg acctggcgcc | 2580 |
| ccccgccggc accaccgacg ccgcgcaccc gggttactct agagtcgggg cggccggccg | 2640 |
| cttcgagcag acatgataag atacattgat gagtttggac aaaccacaac tagaatgcag | 2700 |
| tgaaaaaaat gctttatttg tgaaatttgt gatgctattg ctttatttgt aaccattata | 2760 |
| agctgcaata aacaagttaa caacaacaat tgaatgcctc gcgctttctc tctgctcttg | 2820 |
| tttttggtaa gctggagtca cgggagacca gggactctca ccctcacccc agtgactctt | 2880 |
| aaccggggta ctcgacctgc agccaagcta gcttggctgg acgtaaactc ctcttcagac | 2940 |
| ctaataactt cgtatagcat acattatacg aagttatatt aagggttatt gaatatgatc | 3000 |
| ggaattcctc gacggatccg aacaaacgac ccaacacccg tgcgttttat tctgtctttt | 3060 |
| tattgccgat cccctcagaa gaactcgtca agaaggcgat agaaggcgat gcgctgcgaa | 3120 |
| tcgggagcgg cgataccgta agcacgagg aagcggtcag cccattcgcc gccaagctct | 3180 |
| tcagcaatat cacgggtagc caacgctatg tcctgatagc ggtccgccac acccagccgg | 3240 |
| ccacagtcga tgaatccaga aaagcggcca ttttccacca tgatattcgg caagcaggca | 3300 |
| tcgccatggg tcacgacgag atcctcgccg tcgggcatgc gcgccttgag cctggcgaac | 3360 |
| agttcggctg gcgcgagccc ctgatgctct tcgtccagat catcctgatc gacaagaccg | 3420 |
| gcttccatcc gagtacgtgc tcgctcgatg cgatgtttcg cttggtggtc gaatgggcag | 3480 |

-continued

```
gtagccggat caagcgtatg cagccgccgc attgcatcag ccatgatgga tactttctcg    3540
gcaggagcaa ggtgagatga caggagatcc tgccccggca cttcgcccaa tagcagccag    3600
tcccttcccg cttcagtgac aacgtcgagc acagctgcg aaggaacgcc cgtcgtggcc     3660
agccacgata gccgcgctgc ctcgtcctgc agttcattca gggcaccgga caggtcggtc    3720
ttgacaaaaa gaaccgggcg cccctgcgct gacagccgga cacgcggc atcagagcag     3780 ccgattgtct gttgtgccca gtcatagccg aatagcctct ccacccaagc ggccggagaa   3840
cctgcgtgca atccatcttg ttcaatggcc gatcccatgg taaaaaccct cctcgcaggg   3900
tcgctcggtg ttcgaggcca cacgcgtcac cttaatatgc gaagtggacc tgggaccgcg   3960
ccgccccgac tgcatctgcg tgttcgaatt cgccaatgac aagacgctgg gcggggtttg   4020
ctcgacattg ggtggaaaca ttccaggcct gggtggagag gcttttttgct tcctcttgca   4080 aaaccacact gctcgacatt gggtggaaac attccaggcc tgggtggaga ggcttttttgc   4140 ttcctcttga aaaccacact gctcgacctg cagccaagct agcttggctg acgtaaact    4200 cctcttcaga cctaataact tcgtatagca tacattatac gaagttatat taaggttat    4260 tgaatatgat cggaattcct cgattaagag caggatattt tgttgtgtgg ggctttctgt   4320
gcgttatatg tgtgattagca gaactgatga cctccctgca gggttctgcc ttgtggtggg   4380
aagggtggat tttaagtgct ttgtgaagag tcgttcatct ggctcctgaa aggggctca    4440 aacaggcacc acgtagcatc caatgaagtt tgctttctct gacttccatt gtactgtgag   4500
gttggaatat aacattgcgg ttgccataag gcaccaccag ataatggcac acggtgatat   4560
atagaaattc tagccccttg agatgatcct cttcttactt ttaaaatcaa tagttttgaac  4620 caacaaaagg accctataaa ccaaaagcaa gacaacacga ttcaggacta aactttgcta   4680
tctctttctt gacccaatcc agttctcctc gctggagaga gcacagcttg gtactacaat   4740
gcctccagtg agctcatgac gtatgatgaa gccagtgcat actgtcagcg ggactacaca   4800
catctggtgg caattcagaa caaggaagag atcaactacc ttaactccaa tctgaaacat   4860
tcaccgagtt actactggat tggaatcaga aaagtcaata acgtatggat ctgggtgggg   4920
acggggaagc ctctgacaga ggaagctcag aactgggctc caggtgaacc aaacaacaaa   4980
caaagaaatg aggactgtgt agagatttac atccaacgaa ccaaagactc gggcatgtgg   5040
aatgacgaga gatgtaacaa aaagaagctg gctctgtgct acacaggtat gaagtttctg   5100
catggtggaa ggctggctct gtgtggaggc agcctgacag attgagagtt gtataaagga   5160
attggtctct actagttttt tcaaagagat gattataagt gattttaata gtaattgcat   5220
ctcttagtac tgatttgtgt gagtagaggc aagatatata catatatgtg tgtgtgtatg   5280
tatgtactta tatgtataca tataataatt ctatcaatat acagagtata tatatttgca   5340
taaaaataaa atatgtggtt tagttgtagc tattctgatg tgtatttatt accaccaaaa   5400
tatacaacag atgagactgg aacttgtatc tggcatgcca atcaaaatct ccagcactaa   5460
tgtcattaga gtcatctgga ttgcactgat tctaaattac aaacaaacaa actcatgatg   5520
agcaccatac taattgactg tcctcatatg gactgtgttt tctgtagctt cgtgtaccaa   5580
tgcatcctgc agtggtcatg gtgaatgcat agagaccatc aatagttaca cctgcaagtg   5640
ccaccctggc ttcctgggac ccaactgtga gcaaggtaag tcttgtcctc acctgtttct   5700
tctccaagat ggtaacaccc tctcctcccc cagatggctt gtgatggctt gtcagtcggg   5760
cccatgtgtt tcctctactg agtaagagtg atatagtggc tgagactatg agatcagatc   5820
```

-continued

| | |
|---|---|
| ctcctgggtc aaactgcaga cctactaccc gtattactta tggcaccttg acaaagtagt | 5880 |
| cctgtagggt gactgacgat tccagttgtc atgaaactaa ataacatcat gtggcaatta | 5940 |
| gctgaagctt agcgttttag ttccagagaa cgacaaagaa actgtttcat agtctgatgg | 6000 |
| ttccatagag cctggaccac aggaaatgtt caatgggtga taattatggt gaccagcgtt | 6060 |
| cctctctcag atgcaaaggg agagatgagc agacgtgtgt cttgattcgt tgttttgttt | 6120 |
| gattttcag ctgtgacttg caaccacag gaacaccctg actatggaag cctgaactgc | 6180 |
| tcccacccgt tcggcccctt cagctataat tcctcctgct cctttggctg taaaaggggc | 6240 |
| tacctgccca gcagcatgga gaccaccgtg cggtgtacgt cctctggaga gtggagtgcg | 6300 |
| cctgctccag cctgccatgg taactctccc aatgcagtaa acctcttcac tcctcctcat | 6360 |
| tgccttaatc gaattcctgc agcccggggg atccactagt tctagagc | 6408 |

<210> SEQ ID NO 10
<211> LENGTH: 6314
<212> TYPE: DNA
<213> ORGANISM: Artificial Sequence
<220> FEATURE:
<223> OTHER INFORMATION: TARGETING SEQUENCE

<400> SEQUENCE: 10

| | |
|---|---|
| cgataagctt gatttagcat ataatcagcg gtctaggtca ctaagtaggt actgtgtcac | 60 |
| tacagatacc atattaccac tgttgaaacg agaaatctag tatgaataga acatgagaag | 120 |
| aaacattcag gaatgactcc cctgcacccc agtgcctgtt aggatggcct aaggtagcag | 180 |
| tgactgagca gaaccttggc actgatgtac gtatcatcaa cagttatcca caagaaaatc | 240 |
| gagagtgaca gatcatgggt aataaaatac tcttagtttg ctcatctttg tgaaaccaag | 300 |
| ttctacactt gattgataat ggtaattaga ctttataaca caagacttaa catcacacac | 360 |
| ttgtatccca tttgataaaa ctgcatacaa atataagagc ccagaaaaag aattaattta | 420 |
| gaggggcaga gtctctgaca tcactatgaa agtgttttaa ctcagtggat attcccagaa | 480 |
| aactttttgg atgcagttga gaatttcctc ttagccagat tttgataata atgtcctatg | 540 |
| actcacagga agccagctcc cctataaaga ggctccagca gaagcagtgc tcagtggtcc | 600 |
| tcgactgact acacagcaaa actgcgagaa gaacggatag agagaagcag gagcaataca | 660 |
| cctaagggat ccaacgccag aacaacaatt ccactgaaca gtaagtgcgg attccgaacc | 720 |
| agaggagcct tgggcccgaa gcatagattt atgtgtgctc acatacgcaa aaaaaaaaa | 780 |
| aaaaagtcat tctgattaaa aaagacctgt ctaaactgtt atagtgttgt aattaatacc | 840 |
| tacattttct ctttgtttaa aatgatgaa atcttaaagt ctgcatttat tctccatgct | 900 |
| agatgcctgt gaaataaggg atgaggtaca ggattctaaa acctcacagc tttgacttaa | 960 |
| atgctgttgt agaaggatgt gagtaacccg cacttagaat ttccttctgt gactaattct | 1020 |
| gcactttctc tcctcaggaa agtttctcca gtctagcgcc tggatgaaag caactgctgg | 1080 |
| agtcaattcg cccaccatgc tgctgctgct gctgctgctg ggcctgaggc tacagctctc | 1140 |
| cctgggcatc atcccagttg aggaggagaa cccggacttc tggaaccgcg aggcagccga | 1200 |
| ggccctgggt gccgccaaga gctgcagcc tgcacagaca gccgccaaga acctcatcat | 1260 |
| cttcctgggc gatgggatgg gggtgtctac ggtgacagct gccaggatcc taaaagggca | 1320 |
| gaagaaggac aaactgggc ctgagatacc cctggccatg gaccgcttcc catatgtggc | 1380 |
| tctgtccaag acatacaatg tagacaaaca tgtgccagac agtggagcca cagccacggc | 1440 |
| ctacctgtgc gggtcaagg gcaacttcca gaccattggc ttgagtgcag ccgcccgctt | 1500 |

-continued

```
taaccagtgc aacacgacac gcggcaacga ggtcatctcc gtgatgaatc gggccaagaa   1560
agcagggaag tcagtgggag tggtaaccac cacacgagtg cagcacgcct cgccagccgg   1620
cacctacgcc cacacggtga accgcaactg gtactcggac gccgacgtgc ctgcctcggc   1680
ccgccaggag gggtgccagg acatcgctac gcagctcatc tccaacatgg acattgacgt   1740
gatcctaggt ggaggccgaa agtacatgtt tcgcatggga accccagacc ctgagtaccc   1800
agatgactac agccaaggtg ggaccaggct ggacgggaag aatctggtgc aggaatggct   1860
ggcgaagcgc cagggtgccc ggtatgtgtg gaaccgcact gagctcatgc aggcttccct   1920
ggacccgtct gtgacccatc tcatgggtct ctttgagcct ggagacatga aatacgagat   1980
ccaccgagac tccacactgg acccctccct gatggagatg acagaggctg ccctgcgcct   2040
gctgagcagg aaccccgcg gcttcttcct cttcgtggag ggtggtcgca tcgaccatgg   2100
tcatcatgaa agcagggctt accgggcact gactgagacg atcatgttcg acgacgccat   2160
tgagagggcg ggccagctca ccagcgagga ggacacgctg agcctcgtca ctgccgacca   2220
ctcccacgtc ttctccttcg gaggctaccc cctgcgaggg agctccatct cgggctggc   2280
ccctggcaag gcccgggaca ggaaggccta cacggtcctc ctatacggaa acggtccagg   2340
ctatgtgctc aaggacggcg cccggccgga tgttaccgag agcgagagcg ggagccccga   2400
gtatcggcag cagtcagcag tgcccctgga cgaagagacc cacgcaggcg aggacgtggc   2460
ggtgttcgcg cgcggcccgc aggcgcacct ggttcacggc gtgcaggagc agaccttcat   2520
agcgcacgtc atggccttcg ccgcctgcct ggagccctac accgcctgcg acctggcgcc   2580
ccccgccggc accaccgacg ccgcgcaccc gggttactct agagtcgggg cggccggccg   2640
cttcgagcag acatgataag atacattgat gagtttggac aaaccacaac tagaatggaa   2700
tgcctcgcgc tttctctctg ctcttgtttt tggtaagctg gagtcacggg agaccaggga   2760
ctctcaccct caccccagtg actcttaacc ggggtactcg acctgcagcc aagctagctt   2820
ggctggacgt aaactcctct tcagacctaa taacttcgta tagcatacat tatacgaagt   2880
tatattaagg gttattgaat atgatcggaa ttcctcgacg gatccgaaca aacgacccaa   2940
cacccgtgcg tttattctg tctttttatt gccgatcccc tcagaagaac tcgtcaagaa   3000
ggcgatagaa ggcgatgcgc tgcgaatcgg gagcggcgat accgtaaagc acgaggaagc   3060
ggtcagccca ttcgccgcca agctcttcag caatatcacg ggtagccaac gctatgtcct   3120
gatagcggtc cgccacaccc agccggccac agtcgatgaa tccagaaaag cggccatttt   3180
ccaccatgat attcggcaag caggcatcgc catgggtcac gacgagatcc tcgccgtcgg   3240
gcatgcgcgc cttgagcctg gcgaacagtt cggctggcgc gagcccctga tgctcttcgt   3300
ccagatcatc ctgatcgaca agaccggctt ccatccgagt acgtgctcgc tcgatgcgat   3360
gtttcgcttg gtggtcgaat gggcaggtag ccggatcaag cgtatgcagc cgccgcattg   3420
catcagccat gatggatact ttctcggcag gagcaaggtg agatgacagg agatcctgcc   3480
ccggcacttc gcccaatagc agccagtccc ttcccgcttc agtgacaacg tcgagcacag   3540
ctgcgcaagg aacgcccgtc gtggccagcc acgatagccg cgctgcctcg tcctgcagtt   3600
cattcagggc accggacagg tcggtcttga caaaaagaac cgggcgcccc tgcgctgaca   3660
gccggaacac ggcggcatca gagcagccga ttgtctgttg tgcccagtca tagccgaata   3720
gcctctccac ccaagcggcc ggagaacctg cgtgcaatcc atcttgttca atggccgatc   3780
ccatggtaaa aaccctcctc gcagggtcgc tcggtgttcg aggccacacg cgtcacctta   3840
```

```
atatgcgaag tggacctggg accgcgccgc cccgactgca tctgcgtgtt cgaattcgcc    3900
aatgacaaga cgctgggcgg ggtttgctcg acattgggtg gaaacattcc aggcctgggt    3960
ggagaggctt tttgcttcct cttgcaaaac cacactgctc gacattgggt ggaaacattc    4020
caggcctggg tggagaggct ttttgcttcc tcttgaaaac cacactgctc gacctgcagc    4080
caagctagct tggctggacg taaactcctc ttcagaccta taacttcgt atagcataca     4140 ttatcgaag ttatattaag ggttattgaa tatgatcgga attcctcgat taagagcagg    4200
atattttgtt gtgtggggct ttctgtgcgt tatatggtga ttagcagaac tgatgacctc    4260
cctgcagggt tctgccttgt ggtgggaagg gtggatttta agtgctttgt gaagagtcgt    4320
tcatctggcc cctgaaaggg ggctcaaaca ggcaccacgt agcatccaat gaagtttgct    4380
ttctctgact tccattgtac tgtgaggttg aatataaca ttgcggttgc cataaggcac     4440
caccagataa tggcacacgg tgatatatag aaattctagc cccttgagat gatcctcttc    4500
ttacttttaa aatcaatagt ttgaaccaac aaaaggaccc tataaaccaa aagcaagaca    4560
acacgattca ggactaaact ttgctatctc tttcttgacc caatccagtt ctcctcgctg    4620
gagagagcac agcttggtac tacaatgcct ccagtgagct catgacgtat gatgaagcca    4680
gtgcatactg tcagcgggac tacacacatc tggtggcaat tcagaacaag gaagagatca    4740
actaccttaa ctccaatctg aaacattcac cgagttacta ctggattgga atcagaaaag    4800
tcaataacgt atggatctgg gtggggacgg ggaagcctct gacagaggaa gctcagaact    4860
gggctccagg tgaaccaaac aacaaacaaa gaatgagga ctgtgtagag atttacatcc     4920
aacgaaccaa agactcgggc atgtggaatg acgagagatg taacaaaag aagctggctc     4980 tgtgctacac aggtatgaag tttctgcatg gtggaaggc ggctctgtgt ggaggcagcc     5040
tgacagattg agagttgtat aaaggaattg gtctctacta gttttttcaa agagatgatt    5100
ataagtgatt ttaatagtaa ttgcatctct tagtactgat ttgtgtgagt agaggcaaga    5160
tatatacata tatgtgtgtg tgtatgtatg tacttatatg tatacatata ataattctat    5220
caatatacag agtatatata tttgcataaa aataaaatat gtggtttagt tgtagctatt    5280
ctgatgtgta tttattacca ccaaaatata caacagatga gactggaact tgtatctggc    5340
atgccaatca aaatctccag cactaatgtc attagagtca tctggattgc actgattcta    5400
aattacaaac aaacaaactc atgatgagca ccatactaat tgactgtcct catatggact    5460
gtgttttctg tagcttcgtg taccaatgca tcctgcagtg gtcatggtga atgcatagag    5520
accatcaata gttacacctg caagtgccac cctggcttcc tgggacccaa ctgtgagcaa    5580
ggtaagtctt gtcctcacct gtttcttctc caagatggta acaccctctc ctcccccaga    5640
tggcttgtga tggcttgtca gtcgggccca tgtgtttcct ctactgagta agagtgatat    5700
agtggctgag actatgagat cagatcctcc tgggtcaaac tgcagaccta ctacccgtat    5760
tacttatggc accttgacaa agtagtcctg tagggtgact gacgattcca gttgtcatga    5820
aactaaataa catcatgtgg caattagctg aagcttagcg ttttagttcc agagaacgac    5880
aaagaaactg tttcatagtc tgatggttcc atagagcctg gaccacagga aatgttcaat    5940
gggtgataat tatggtgacc agcgttcctc tctcagatgc aaagggagag atgagcagac    6000
gtgtgtcttg attcgttgtt ttgtttgatt tttcagctgt gacttgcaaa ccacaggaac    6060
accctgacta tggaagcctg aactgctccc accgttcgg cccttcagc tataattcct       6120 cctgctcctt tggctgtaaa aggggctacc tgccagcag catggagacc accgtgcggt    6180
gtacgtcctc tggagagtgg agtgcgcctg ctccagcctg ccatggtaac tctcccaatg    6240
```

```
cagtaaacct cttcactcct cctcattgcc ttaatcgaat tcctgcagcc cggggggatcc    6300 actagttcta gagc                                                       6314

<210> SEQ ID NO 11
<211> LENGTH: 5083
<212> TYPE: DNA
<213> ORGANISM: Artificial Sequence
<220> FEATURE:
<223> OTHER INFORMATION: DNA CONSTRUCT

<400> SEQUENCE: 11
ttagcatata atcagcggtc taggtcacta agtaggtact gtgtcactac agataccata      60
ttaccactgt tgaaacgaga aatctagtat gaatagaaca tgagaagaaa cattcaggaa     120
tgactcccct gcaccccagt gcctgttagg atggcctaag gtagcagtga ctgagcagaa     180
ccttggcact gatgtacgta tcatcaacag ttatccacaa gaaatcgag agtgacagat      240 catgggtaat aaaatactct tagtttgctc atctttgtga aaccaagttc tacacttgat     300
tgataatggt aattagactt tataacacaa gacttaacat cacacacttg tatcccattt     360
gataaaactg catacaaata taagagccca gaaaagaat  taatttagag gggcagagtc     420
tctgacatca ctatgaaagt gttttaactc agtggatatt cccagaaaac tttttggatg     480
cagttgagaa tttcctctta gccagatttt gataataatg tcctatgact cacaggaagc     540
cagctcccct ataagaggc tccagcgaaa gcagtgctca gtggtcctcg actgactaca      600
cagcaaaact gcgagaagaa cggatagaga gaagcaggag caatacacct aagggatcca     660
acgccagaac aacaattcca ctgaacagta agtgcggatt ccgaaccaga ggagccttgg     720
gcccgaagca tagatttatg tgtgctcaca tacgcaaaaa aaaaaaaaaa aagtcattct     780
gattaaaaaa gacctgtcta aactgttata gtgttgtaat taatacctac attttctctt     840
tgtttaaaat gatggaaatc ttaaagtctg catttattct ccatgctaga tgcctgtgaa     900
ataagggatg aggtacagga ttctaaaacc tcacagcttt gacttaaatg ctgttgtaga     960
aggatgtgag taacccgcac ttagaatttc cttctgtgac taattctgca ctttctctcc    1020
tcaggaaagt ttctccagtc tagcgcctgg atgaaagcaa ctgctggagt caattcgccc    1080
accatgctgc tgctgctgct gctgctgggc ctgaggctac agctctccct gggcatcatc    1140
ccagttgagg aggagaaccc ggacttctgg aaccgcgagg cagccgaggc cctgggtgcc    1200
gccaagaagc tgcagcctgc acagacagcc gccaagaacc tcatcatctt cctggcgat    1260 gggatggggg tgtctacggt gacagctgcc aggatcctaa aagggcagaa gaaggacaaa    1320
ctggggcctg agataccccct ggccatggac cgcttcccat atgtggctct gtccaagaca    1380
tacaatgtag acaaacatgt gccagacagt ggagccacag ccacggccta cctgtgcggg    1440
gtcaagggca acttccagac cattggcttg agtgcagccg cccgctttaa ccagtgcaac    1500
acgacacgcg gcaacgaggt catctccgtg atgaatcggg ccaagaaagc agggaagtca    1560
gtgggagtgg taaccaccac acgagtgcag cacgcctcgc cagccggcac ctacgcccac    1620
acggtgaacc gcaactggta ctcggacgcc gacgtgcctg cctcggcccg ccaggagggg    1680
tgccaggaca tcgctacgca gctcatctcc aacatggaca ttgacgtgat cctaggtgga    1740
ggccgaaagt acatgttccg catgggaacc ccagaccctg agtacccaga tgactacagc    1800
caaggtggga ccaggctgga cgggaagaat ctggtgcagg aatggctggc gaagcgccag    1860
ggtgcccggt atgtgtggaa ccgcactgag ctcatgcagg cttccctgga cccgtctgtg    1920
```

-continued

```
acccatctca tgggtctctt tgagcctgga gacatgaaat acgagatcca ccgagactcc    1980
acactggacc cctccctgat ggagatgaca gaggctgccc tgcgcctgct gagcaggaac    2040
ccccgcggct tcttcctctt cgtggagggt ggtcgcatcg accatggtca tcatgaaagc    2100
agggcttacc gggcactgac tgagacgatc atgttcgacg acgccattga gagggcgggc    2160
cagctcacca gcgaggagga cacgctgagc ctcgtcactg ccgaccactc ccacgtcttc    2220
tccttcggag gctacccccct gcgagggagc tccatcttcg ggctggcccc tggcaaggcc    2280
cgggacagga aggcctacac ggtcctccta tacggaaacg gtccaggcta tgtgctcaag    2340
gacggcgccc ggccggatgt taccgagagc gagagcggga gccccgagta tcggcagcag    2400
tcagcagtgc ccctggacga agagacccac gcaggcgagg acgtggcggt gttcgcgcgc    2460
ggcccgcagg cgcacctggt tcacggcgtg caggagcaga ccttcatagc gcacgtcatg    2520
gccttcgccg cctgcctgga gccctacacc gcctgcgacc tggcgccccc cgccggcacc    2580
accgacgccg cgcacccggg ttactctaga gtcgggggcgg ccggccgctt cgagcagaca    2640
tgataagata cattgatgag tttggacaaa ccacaactag aatgcagtga aaaaatgct    2700 ttatttgtga aatttgtgat gctattgctt tatttgtaac cattataagc tgcaataaac    2760
aagttaacaa caacaattga atgcctcgcg ctttctctct gctcttgttt ttggtaagct    2820
ggagtcacgg gagaccaggg actctcaccc tcaccccagt gactcttaac cggggtactc    2880
gacctgcagc caagctagct tggctggacg taaactcctc ttcagaccta ataacttcgt    2940
atagcataca ttatacgaag ttatattaag ggttattgaa tatgatcgga attcctcgat    3000
taagagcagg atattttgtt gtgtggggct ttctgtgcgt tatatggtga ttagcagaac    3060
tgatgacctc cctgcagggt tctgccttgt ggtgggaagg gtggatttta agtgctttgt    3120
gaagagtcgt tcatctggct cctgaaaggg ggctcaaaca ggcaccacgt agcatccaat    3180
gaagtttgct ttctctgact tccattgtac tgtgaggttg aatataaca ttgcggttgc    3240 cataaggcac caccagataa tggcacacgg tgatatatag aaattctagc cccttgagat    3300
gatcctcttc ttacttttaa aatcaatagt ttgaaccaac aaaaggaccc tataaaccaa    3360
aagcaagaca acacgattca ggactaaact ttgctatctc tttcttgacc caatccagtt    3420
ctcctcgctg gagagagcac agcttggtac tacaatgcct ccagtgagct catgacgtat    3480
gatgaagcca gtgcatactg tcagcgggac tacacacatc tggtggcaat tcagaacaag    3540
gaagagatca actaccttaa ctccaatctg aaacattcac cgagttacta ctggattgga    3600
atcagaaaag tcaataacgt atggatctgg gtggggacgg ggaagcctct gacagaggaa    3660
gctcagaact gggctccagg tgaaccaaac aacaaacaaa gaaatgagga ctgtgtagag    3720
atttacatcc aacgaaccaa agactcgggc atgtggaatg acgagagatg taacaaaaag    3780
aagctggctc tgtgctacac aggtatgaag tttctgcatg gtggaaggct ggctctgtgt    3840
ggaggcagcc tgacagattg agagttgtat aaaggaattg gtctctacta gttttttcaa    3900
agagatgatt ataagtgatt ttaatagtaa ttgcatctct tagtactgat ttgtgtgagt    3960
agaggcaaga tatatacata tatgtgtgtg tgtatgtatg tacttatatg tatacatata    4020
ataattctat caatatacag agtatatata tttgcataaa aataaaatat gtggtttagt    4080
tgtagctatt ctgatgtgta tttattacca ccaaaatata caacagatga gactggaact    4140
tgtatctggc atgccaatca aaatctccag cactaatgtc attagagtca tctggattgc    4200
actgattcta aattacaaac aaacaaactc atgatgagca ccatactaat tgactgtcct    4260
catatggact gtgttttctg tagcttcgtg taccaatgca tcctgcagtg gtcatggtga    4320
```

-continued

| | |
|---|---|
| atgcatagag accatcaata gttacacctg caagtgccac cctggcttcc tgggacccaa | 4380 |
| ctgtgagcaa ggtaagtctt gtcctcacct gtttcttctc caagatggta acaccctctc | 4440 |
| ctcccccaga tggcttgtga tggcttgtca gtcgggccca tgtgtttcct ctactgagta | 4500 |
| agagtgatat agtggctgag actatgagat cagatcctcc tgggtcaaac tgcagaccta | 4560 |
| ctaccgtat tacttatggc accttgacaa gtagtcctg tagggtgact gacgattcca | 4620 |
| gttgtcatga aactaaataa catcatgtgg caattagctg aagcttagcg ttttagttcc | 4680 |
| agagaacgac aaagaaactg tttcatagtc tgatggttcc atagagcctg gaccacagga | 4740 |
| aatgttcaat gggtgataat tatggtgacc agcgttcctc tctcagatgc aaagggagag | 4800 |
| atgagcagac gtgtgtcttg attcgttgtt ttgtttgatt tttcagctgt gacttgcaaa | 4860 |
| ccacaggaac ccctgacta tggaagcctg aactgctccc accgttcgg ccccttcagc | 4920 |
| tataattcct cctgctcctt tggctgtaaa aggggctacc tgcccagcag catggagacc | 4980 |
| accgtgcggt gtacgtcctc tggagagtgg agtgcgcctg ctccagcctg ccatggtaac | 5040 |
| tctcccaatg cagtaaaacct cttcactcct cctcattgcc tta | 5083 |

<210> SEQ ID NO 12
<211> LENGTH: 4989
<212> TYPE: DNA
<213> ORGANISM: Artificial Sequence
<220> FEATURE:
<223> OTHER INFORMATION: DNA CONSTRUCT

<400> SEQUENCE: 12

| | |
|---|---|
| ttagcatata atcagcggtc taggtcacta agtaggtact gtgtcactac agataccata | 60 |
| ttaccactgt tgaaacgaga aatctagtat gaatagaaca tgagaagaaa cattcaggaa | 120 |
| tgactcccct gcaccccagt gcctgttagg atggcctaag gtagcagtga ctgagcagaa | 180 |
| ccttggcact gatgtacgta tcatcaacag ttatccacaa gaaaatcgag agtgacagat | 240 |
| catgggtaat aaaatactct tagttttgctc atctttgtga aaccaagttc tacacttgat | 300 |
| tgataatggt aattagactt tataacacaa gacttaacat cacacacttg tatcccattt | 360 |
| gataaaactg catacaaata taagagccca gaaaagaat taatttagag gggcagagtc | 420 |
| tctgacatca ctatgaaagt gttttaactc agtggatatt cccagaaaac ttttttggatg | 480 |
| cagttgagaa tttcctctta gccagatttt gataataatg tcctatgact cacaggaagc | 540 |
| cagctcccct ataaagaggc tccagcagaa gcagtgctca gtggtcctcg actgactaca | 600 |
| cagcaaaact gcgagaagaa cggatagaga gaagcaggag caatacacct aagggatcca | 660 |
| acgccagaac aacaattcca ctgaacagta agtgcggatt ccgaaccaga ggagccttgg | 720 |
| gcccgaagca tagatttatg tgtgctcaca tacgcaaaaa aaaaaaaaaa aagtcattct | 780 |
| gattaaaaaa gacctgtcta aactgttata gtgttgtaat taatacctac attttctctt | 840 |
| tgtttaaaat gatggaaatc ttaaagtctg catttattct ccatgctaga tgcctgtgaa | 900 |
| ataagggatg aggtacagga ttctaaaacc tcacagcttt gacttaaatg ctgttgtaga | 960 |
| aggatgtgag taacccgcac ttagaatttc cttctgtgac taattctgca ctttctctcc | 1020 |
| tcaggaaagt ttctccagtc tagcgcctgg atgaaagcaa ctgctggagt caattcgccc | 1080 |
| accatgctgc tgctgctgct gctgctgggc ctgaggctac agctctccct gggcatcatc | 1140 |
| ccagttgagg aggagaaccc ggacttctgg aaccgcgagg cagccgaggc cctggtgcc | 1200 |
| gccaagaagc tgcagcctgc acagacagcc gccaagaacc tcatcatctt cctgggcgat | 1260 |

-continued

```
gggatggggg tgtctacggt gacagctgcc aggatcctaa aagggcagaa gaaggacaaa    1320
ctggggcctg agatacccct ggccatggac cgcttcccat atgtggctct gtccaagaca    1380
tacaatgtag acaaacatgt gccagacagt ggagccacag ccacggccta cctgtgcggg    1440
gtcaagggca acttccagac cattggcttg agtgcagccg cccgctttaa ccagtgcaac    1500
acgacacgcg gcaacgaggt catctccgtg atgaatcggg ccaagaaagc agggaagtca    1560
gtgggagtgg taaccaccac acgagtgcag cacgcctcgc cagccggcac ctacgcccac    1620
acggtgaacc gcaactggta ctcggacgcc gacgtgcctg cctcggcccg ccaggagggg    1680
tgccaggaca tcgctacgca gctcatctcc aacatggaca ttgacgtgat cctaggtgga    1740
ggccgaaagt acatgtttcg catgggaacc ccagaccctg agtacccaga tgactacagc    1800
caaggtggga ccaggctgga cgggaagaat ctggtgcagg aatggctggc gaagcgccag    1860
ggtgcccggt atgtgtggaa ccgcactgag ctcatgcagg cttccctgga cccgtctgtg    1920
acccatctca tgggtctctt tgagcctgga gacatgaaat acgagatcca ccgagactcc    1980
acactggacc cctccctgat ggagatgaca gaggctgccc tgcgcctgct gagcaggaac    2040
ccccgcggct tcttcctctt cgtggagggt ggtcgcatcg accatggtca tcatgaaagc    2100
agggcttacc gggcactgac tgagacgatc atgttcgacg acgccattga gagggcgggc    2160
cagctcacca gcgaggagga cacgctgagc ctcgtcactg ccgaccactc ccacgtcttc    2220
tccttcggag gctacccct gcgagggagc tccatcttcg gctggcccc tgcaaggcc     2280
cgggacagga aggcctacac ggtcctccta tacgaaacg gtccaggcta tgtgctcaag    2340
gacggcgccc ggccggatgt taccgagagc gagagcggga ccccgagta tcggcagcag    2400
tcagcagtgc ccctggacga agagaccac gcaggcgagg acgtggcggt gttcgcgcgc    2460
ggcccgcagg cgcacctggt tcacggcgtg caggagcaga ccttcatagc gcacgtcatg    2520
gccttcgccg cctgcctgga gccctacacc gcctgcgacc tggcgccccc cgccggcacc    2580
accgacgccg cgcacccggg ttactctaga gtcggggcgg ccggccgctt cgagcagaca    2640
tgataagata cattgatgag tttggacaaa ccacaactag aatggaatgc ctcgcgcttt    2700
ctctctgctc ttgtttttgg taagctggag tcacgggaga ccaggactc tcaccctcac    2760
cccagtgact cttaaccggg gtactcgacc tgcagccaag ctagcttggc tggacgtaaa    2820
ctcctcttca gacctaataa cttcgtatag catacattat acgaagttat attaagggtt    2880
attgaatatg atcggaattc ctcgattaag agcaggatat tttgttgtgt ggggcttttct  2940
gtgcgttata tggtgattag cagaactgat gacctccctg cagggttctg ccttgtggtg    3000
ggaagggtgg attttaagtg cttgtgaag agtcgttcat ctggctcctg aaaggggggct   3060
caaacaggca ccacgtagca tccaatgaag tttgctttct ctgacttcca ttgtactgtg    3120
aggttggaat ataacattgc ggttgccata aggcaccacc agataatggc acacggtgat    3180
atatagaaat tctagcccct tgagatgatc ctcttcttac ttttaaaatc aatagtttga    3240
accaacaaaa ggaccctata aaccaaaagc aagacaacac gattcaggac taaactttgc    3300
tatctctttc ttgacccaat ccagttctcc tcgctggaga gagcacagct tggtactaca    3360
atgcctccag tgagctcatg acgtatgatg aagccagtgc atactgtcag cgggactaca    3420
cacatctggt ggcaattcag aacaaggaag agatcaacta ccttaactcc aatctgaaac    3480
attcaccgag ttactactgg attggaatca gaaaagtcaa taacgtatgg atctgggtgg    3540
ggacggggaa gcctctgaca gaggaagctc agaactgggc tccaggtgaa ccaaacaaca    3600
aacaaagaaa tgaggactgt gtagagattt acatccaacg aaccaaagac tcgggcatgt    3660
```

```
ggaatgacga gagatgtaac aaaaagaagc tggctctgtg ctacacaggt atgaagtttc    3720
tgcatggtgg aaggctggct ctgtgtggag gcagcctgac agattgagag ttgtataaag    3780
gaattggtct ctactagttt tttcaaagag atgattataa gtgattttaa tagtaattgc    3840
atctcttagt actgatttgt gtgagtagag gcaagatata tacatatatg tgtgtgtgta    3900
tgtatgtact tatatgtata catataataa ttctatcaat atacagagta tatatatttg    3960
cataaaaata aaatatgtgg tttagttgta gctattctga tgtgtattta ttaccaccaa    4020
aatatacaac agatgagact ggaacttgta tctggcatgc caatcaaaat ctccagcact    4080
aatgtcatta gagtcatctg gattgcactg attctaaatt acaaacaaac aaactcatga    4140
tgagcaccat actaattgac tgtcctcata tggactgtgt tttctgtagc ttcgtgtacc    4200
aatgcatcct gcagtggtca tggtgaatgc atagagacca tcaatagtta cacctgcaag    4260
tgccaccctg gcttcctggg acccaactgt gagcaaggta agtcttgtcc tcacctgttt    4320
cttctccaag atggtaacac cctctcctcc cccagatggc ttgtgatggc ttgtcagtcg    4380
ggcccatgtg tttcctctac tgagtaagag tgatatagtg gctgagacta tgagatcaga    4440
tcctcctggg tcaaactgca gacctactac ccgtattact tatggcacct tgacaaagta    4500
gtcctgtagg gtgactgacg attccagttg tcatgaaact aaataacatc atgtggcaat    4560
tagctgaagc ttagcgtttt agttccagag aacgacaaag aaactgtttc atagtctgat    4620
ggttccatag agcctggacc acaggaaatg ttcaatgggt gataattatg gtgaccagcg    4680
ttcctctctc agatgcaaag ggagagatga gcagacgtgt gtcttgattc gttgttttgt    4740
ttgatttttc agctgtgact tgcaaaccac aggaacaccc tgactatgga agcctgaact    4800
gctcccaccc gttcggcccc ttcagctata attcctcctg ctcctttggc tgtaaaaggg    4860
gctacctgcc cagcagcatg gagaccaccg tgcggtgtac gtcctctgga gagtggagtg    4920
cgcctgctcc agcctgccat ggtaactctc ccaatgcagt aaacctcttc actcctcctc    4980
attgcctta                                                           4989
```

TRANSGENIC ANIMALS FOR STUDYING REGULATION OF GENES

BACKGROUND OF THE INVENTION

Vascular endothelial cell (EC) activation is one of the first events in inflammatory conditions and transplant rejection. A specific marker of EC activation is E-selectin. Expression of this gene is generally absent under resting conditions and induced by inflammatory stimuli, as well as being NF-kB dependent. Expression is restricted to the endothelium.

Immunohistochemistry is a standard technique by which signalling events involved in disorders associated with inflammatory, thrombotic, ischaemic or neoplastic conditions or transplant rejection, can be assessed; and, for example, E-selectin expression can be readily studied by this method in vitro. However, monitoring of E-selectin expression in vivo has been limited to immunohistochemistry of biopsies or post-mortem specimens. There has been a need by workers in the art for an in vivo model allowing assessment of E-selectin expression in a live subject.

SUMMARY OF THE INVENTION

The present invention relates to an animal model useful for screening potential therapeutic agents for the treatment of disorders associated with inflammatory, thrombotic, ischaemic or neoplastic conditions or prevention of transplant rejection. In particular, the present invention provides a novel model in which endothelial cell activation can be assessed in vivo by a simple and sensitive enzyme assay.

BRIEF DESCRIPTION OF THE DRAWINGS

FIG. 1 (bottom panel) schematically depicts the SEAP-1 and SEAP-2 messenger RNAs. In all of the figures, genetic constructs are conventionally depicted with the 5' terminus at left.

FIG. 2(a) ("Endogenous E-selectin locus.") schematically depicts the E-selectin targeting constructs prepared in Examples 1 and 2 for carrying out homologous recombination in murine embryonic stem cells. Said constructs comprise the SEAP-1 gene (or the SEAP-2 gene fused to the SV40 late mRNA polyadenylation site) inserted into the mutagenized start site (ATG) of the E-selectin gene, together with a NeoR gene flanked by loxP sites. FIG. 2(b) ("Targeted locus.") depicts the heterologous E-selectin allele (the "targeted locus") (also referred to as the "knock in allele") resulting from integration of the targeted construct into the murine chromosomal E-selectin allele. FIG. 2(c) ("Targeted locus after Cre-mediated neo cassette removal.") shows the targeted locus following Cre-mediated removal of the neo casette and one of the LoxP sites.

FIG. 6 shows the localization of SEAP expression by alkaline phosphatase histochemistry performed on cryosections from tongues of SEAP-2 mice 6 hours after saline ("SEAP-2 control") or LPS injection ("SEAP-2 LPS"). The panels marked "LPS" show the immunolocalization of E-selectin in LPS treated mice. Arrows point to stained vessels.

DETAILED DESCRIPTION

Figure 1:
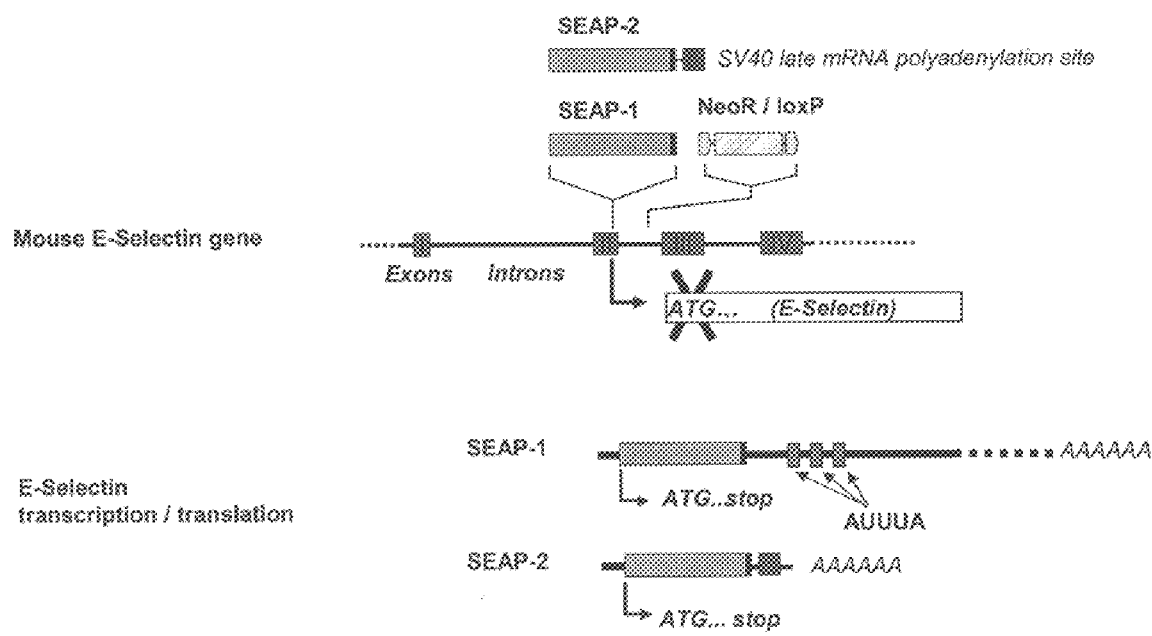
FIG. 1 (top panel) schematically illustrates the strategy which is pursued in Examples 1 and 2 for targeted replacement of the native mouse E-selectin allele with secreted alkaline phosphatase (SEAP). The SEAP-1 gene, or the SEAP-2 gene fused to the SV40 late mRNA polyadenylation site, is inserted into the mutagenized start site (ATG) of the E-selectin gene, together with a Neo R/loxP fragment.

The present invention provides in a first aspect a transgenic non-human animal wherein expression of an exogenous soluble marker specifically by endothelial cells, e.g., vascular endothelial cells, is regulatable by a chemical stimulus, including a cytokine, or a physical stimulus including light or temperature.

In particular, the invention comprises a transgenic non-human animal comprising a polynucleotide encoding a soluble marker protein functionally linked to a regulatory sequence of an endogenous gene encoding E-selectin.

The soluble marker protein is preferably an exogenous protein, i.e. which is not normally produced by the animal. Alternatively, the protein may be produced by the animal but is not normally under the control of a regulatory sequence of an endogenous gene encoding E-selectin. The protein is selected to be detectable in plasma or blood samples by standard experimental means.

Transgenic non-human animals include animals, e.g., mammals, e.g., pigs, cows, goats, as well as non-human primates, such as monkeys, and rodents, such as mice and rats, into which a suitable DNA construct has been introduced directly, as well as progeny of such animals still retaining said construct. Examples for useful animal lines include any animal line normally kept as laboratory animals. This invention shall also be understood to include in all its aspects somatic recombinant non-human animals. The term "transgenic" refers in general to animals having an exogenous gene (i.e. non-native gene, i.e. transgene), such as a marker gene, in the chromosomal DNA of their germ line; and the term "somatic recombinant" refers to animals having an exogenous gene, such as for example a marker gene, in the DNA of at least a portion of their somatic cells.

Soluble marker proteins of the invention include proteins with or without enzymatic activity which are conveniently secreted either naturally or as a result of genetic manipulation into the extracellular space. Genes encoding suitable plasma-soluble, non-toxic marker proteins are known (e.g., human growth hormone), commercially available (e.g., a modified, secreted heat stable alkaline phosphatase), or may be prepared following established routes of gene identification, isolation, amplification and modification, e.g., ligation.

In preferred embodiments, the soluble marker transgene of the invention is a secreted form of heat-stable human placental alkaline phosphatase gene lacking the membrane anchoring domain, referred to herein as "SEAP" (for "secreted alkaline phosphatase"). Of course, the introduced marker gene need not be limited to the SEAP gene, but may also comprise one or more soluble marker proteins having additional reporter functions.

In its more particular aspects, the invention contemplates a transgenic (or somatic recombinant) non-human animal having inserted in its genome a soluble reporter gene, wherein the soluble reporter gene is under the control of the promoter of an E-selectin gene of a chromosomal E-selectin allele of said animal.

The inserted soluble marker gene can be placed at a variety of positions within the genomic E-selectin sequence, provided that its expression remains under the control of the endogenous E-selectin promoter.

The exogenous soluble marker gene is preferably inserted into the genome of the subject animal by means of a "targeting construct" comprising the marker gene under the control of the native E-selectin promoter of the animal to be rendered transgenic or a somatic recombinant, and optional additional transgenes.

Preferably, the targeting construct is also constructed so that the marker gene or other transgene is inserted in a manner to decrease or prevent (i.e. "knock out") expression of the native E-selectin structural gene.

Most preferably, the genetic construct is inserted at the E-selectin allele transcription initiation site, at the E-selectin allele translation initiation site, or at any position in between.

The targeting construct is generally inserted into the host animal genome by homologous recombination into the wild-type chromosomal E-selectin allele, and therefore can be engineered to recombine at any of a variety of positions in the E-selectin allele so long as the inserted marker gene is positioned such that expression of the soluble marker gene is under the control of the E-selectin promoter.

In a preferred embodiment, the E-selectin gene of the non-human animal is modified, as a result of the homologous recombination, by insertion of the genetic construct at a site which is between the transcription and translation initiation sites of the native E-selectin structural gene of the animal, thereby placing expression of the soluble marker gene under the control of the native E-selectin promotor, while "knocking out" normal expression of the E-selectin structural gene.

The resulting allele, comprising the inserted soluble marker sequence under the control of the native E-selectin promoter, and optional additional transgenes, is often referred to as a "knock-in" allele.

The invention contemplates a transgenic animal that is either homozygous or eterozygous for the knock-in allele.

In its most preferred embodiment, the invention consists of a transgenic mouse that is homozygous or heterozygous for an E-selectin allele having inserted therein a genetic construct comprising a soluble marker gene under the control of the E-selectin promoter, wherein said inserted genetic construct diminishes or prevents expression of the native E-selectin structural gene of that allele. Such a mouse is commonly referred to in the art as a "knock out" mouse.

The targeting construct is preferably constructed so as to assist in homologous recombination of the synthetic sequence with the endogenous gene; and accordingly, will also preferably comprise at least elements of the native structural E-selectin gene.

As indicated above, the targeting construct may comprise additional components such as one or more additional reporters, selection markers such as a neo resistance cassette, and the like. (Upon insertion into the cellular genome of the subject animal, certain selection markers may be excised, for example, by Cre-mediated neo cassette removal.)

Recombinant DNA constructs of the present invention may be prepared according to procedures known in the art, starting from, e.g., a genomic clone. A gene encoding E-selectin and its regulatory sequence may be identified and amplified following procedures known in the art, e.g, by using appropriate primer pairs. Whether one or the other of the methods known in the art for the preparation of the DNA constructs is applied may depend on their intended further use.

The targeting construct of the invention is preferably prepared from an isolated genomic clone of the native E-selectin gene of the subject animal by inserting the marker gene at a suitable position (1) to be under the control of the E-selectin promoter, and (2) to reduce or prevent normal expression of the native structural E-selectin gene.

Preferably, the marker gene itself is inserted between the transcription and translation initiation sites of the isolated genomic E-selectin clone so as to "knock out" normal expression of the endogenous functional E-selectin gene.

In a particular embodiment which is illustrated in Example 1, step (a)(v), the targeting construct comprises, in order from 5' to 3': the native murine E-selectin promoter; a fragment of the native murine structural E-selectin gene comprising exon I; an SEAP-encoding component (comprising a Kozak consensus translation initiating signal, the SEAP coding sequence, and an SV-40 late mRNA polyadenylation signal) cloned into the mutated translational start site, Mfe I, of the murine E-selectin gene in exon II; a neoR cassette (comprising a loxP site; a neoR cassette, and a second LoxP site) cloned into intron II; and an additional fragment of the structural E-selectin gene comprising exons III, IV and V. A species of such a targeting construct has SEQ. ID. NO:9.

In another embodiment of a murine SEAP-targeting construct which is illustrated in Example 2, step (a)(ii), the targeting construct comprises, in order from 5' to 3': the native murine E-selectin promoter; a fragment of the native murine structural E-selectin gene comprising exon I; an SEAP-encoding sequence (comprising a Kozak consensus translation initiating signal and an SEAP coding sequence) cloned into the mutated translational start site, Mfe I, of the murine E-selectin gene in exon II, a neoR cassette (comprising a loxP site; a neoR cassette; and a second loxP site) cloned into intron II; and and exons III, IV and V. A species of such a targeting construct has SEQ. ID. NO:10.

Thus this invention provides a recombinant DNA construct comprising a polynucleotide having a nucleotide sequence as illustrated in SEQ ID NO:9 or SEQ ID NO:10.

Well-established methods for germ-line or somatic insertion of a DNA construct include viral or non-viral vector-mediated gene transfer into fertilized eggs, zygotes or early embryos and/or a specific tissue (such as brain) in the adult animal, e.g., by gene transfer into embryonic stem cells, retroviral infection of early embryos or pronuclear microinjection.

For example, gene transfer into embryonic stem cells may be carried out using a "knock-in" strategy performed, e.g., in two sequential steps: (1) by first generating a recombinant DNA construct (the "targeting construct") comprising a genomic clone of the E-selectin gene having inserted therein an exogenous genetic construct comprising the soluble marker gene of interest; and (2) by transfecting or otherwise inserting the targeting construct into the embryonic stem cells under conditions suitable to effectuate homologous recombination of the targeting construct with the endogenous, chromosomal E-selectin allele.

Identification of successful embryonic stem cell clones may be by, e.g., using the Neo-loxP approach, i.e. by insertion of a Neo resistance cassette carrying the thymidine kinase promoter and Neo cDNA flanked by loxP sites, into an intron of the E-selectin gene. Successfully targeted ES-cell clones may then be transfected with a plasmid expressing the Cre-recombinase, thereby removing the neo-selection cassette (as well as one of the loxP sites in intron II).

Using standard technology for the preparation of a transgenic animal (e.g., a mouse), the insertion of the targeting construct is made in a single allele of the native E-selectin gene, and through genetic crossing, there can thereby be obtained a fertilized egg with the insertion in either a single E-selectin allele, i.e. heterozygous, or in both E-selectin alleles, i.e. homozygous. Further manipulation of resulting fertilized eggs, zygotes or early embryos and breeding of resulting transgenic founder animals follows established routes of breeding transgenic animals. Successful transgenic non-human animals may be identified, e.g., by fur colour, e.g., by the absence of fur colour.

Accordingly, the targeted E-selectin gene ("targeted locus") of Example 1, following Cre-mediated neo cassette removal, is schematically depicted in FIG. 2(c) hereof, and comprises, in order from 5' to 3': the native murine E-selectin promoter; a fragment of the native murine structural E-selectin gene comprising exon I; an SEAP-encoding component (comprising a Kozak consensus translation initiating signal, the SEAP coding sequence, and an SV-40 late mRNA polyadenyl-ation signal) cloned into the mutated translational start site, Mfe I, of the murine E-selectin gene in exon II; a single loxP site in intron II, and an additional fragments of the structural E-selectin gene comprising exons III, IV and V. A species of such a targeting construct has SEQ. ID. NO:11.

Likewise, the targeted E-selectin gene ("targeted locus") of Example 2, following Cre-mediated neo-cassette removal, is also schematically depicted in FIG. 2(c), and comprises, in order from 5' to 3': the native murine E-selectin promoter; a fragment of the native murine structural E-selectin gene comprising exon I; an SEAP-encoding component (comprising a Kozak consensus translation initiating signal and, the SEAP coding sequence) cloned into the mutated translational start site, Mfe I, of the murine E-selectin gene in exon II; a single loxP site in intron II, and an additional fragments of the structural E-selectin gene comprising exons III, IV and V. A species of such a targeting construct has SEQ. ID. NO:12.

Thus this invention also provides a recombinant DNA construct comprising a polynucleotide having SEQ ID NO:11 or SEQ ID NO:12, and a transgenic (or somatic recombinant) non-human animal comprising in its genome a nucleotide sequence having SEQ ID NO:11 or SEQ ID NO:12. Most preferably, the invention consists of a transgenic knockout mouse comprising in its genome SEQ. ID. NO:11 or SEQ. ID. NO:12.

The transgenic or somatic recombinant non-human animals of the invention are useful for readily assessing and non-invasively monitoring in a body fluid, e.g., in plasma, the expression of a marker for E-selectin. An advantage of this model is that the expression of a marker for an inflammatory, thrombotic, ischaemic or neoplastic condition can be followed in an easy and experimentally reproducible system, and time course analyses are possible in this model without killing the animals. For example, this model offers the possibility to assess the specific activation of endothelium in different disease models of e.g., inflammation, angiogenesis, atherosclerosis, thrombosis, and acute or chronic transplant rejection. The model can be used for profiling of compounds inhibiting specific signaling events related to the expression of E-selectin. For example, the model can be used to study the specific effect of inhibitors of the NFkB pathway.

Models based on the transgenic or somatic recombinant non-human animals of the invention may be used for example to identify and assess the efficacy of potential therapeutic agents in disorders associated with inflammatory, thrombotic, ischaemic or neoplastic conditions. In particular such models may be used in screening or characterization assays for detecting agents likely to, e.g., prevent or treat inflammation, angiogenesis, thrombosis and acute or chronic transplant rejection.

Accordingly in a further aspect the invention comprises a method for testing a potential therapeutic agent for a specified condition, in particular a disorder associated with inflammatory, thrombotic, ischaemic or neoplastic conditions or transplant rejection, wherein the agent is administered to the transgenic non-human animal. Moreover the invention comprises a screening or characterization assay consisting in or including such a method.

Methods for testing potential therapeutic agents using animals are well known in the art. The transgenic non-human animals of the invention may be used in analogous manner.

The effects of the potential therapeutic agent may be determined by administering the agent to a transgenic non-human animal, monitoring marker concentration in a body fluid, e.g., plasma, and comparing the result with a result obtained from an untreated transgenic or somatic recombinant non-human animal.

In a further embodiment the present invention is directed to a novel modulator of a regulatable protein identified by a screening assay comprising administering the potential modulator to a transgenic or somatic recombinant non-human animal, monitoring marker concentration in a body fluid, e.g., plasma, and comparing the result with a result obtained from an untreated such animal.

Methods for monitoring marker concentration in a body fluid are well known in the art. For example, concentration of a marker enzyme may be determined by quantifying the enzymatic activity. Marker proteins without enzymatic activity may be quantified by other means e.g., by immunological methods.

The transgenic non-human animals are further useful to monitor disease development and progression in established models of disease involving spontanously developing or induced disease conditions in wild-type or transgenic animals. For this, the transgenic non-human animals may be crossed with animal strains known for their use as animal models. Examples for suitable animal strains include mouse strains, e.g., atherosclerosis prone mice, e.g., targeted disruption of e.g., LDL-R or Apo E; mouse models for inflammation, e.g., mouse strains showing defects in NFκB signalling, defects in TNF and TNF-R, IL-1 and IL-1-R, or mutations such as the MRL-Ipr mouse; mouse strains with immune disorders, e.g., cytokine transgenic or knockout mice; Thrombosis-prone mice, e.g., plasminogen or plasminogen activator deficient mice; and mouse strains which develop tumors. Disease progression may be monitored by e.g., following marker gene expression in the F1 animals or in offsprings resulting from crossing in of the transgenic non-human animals for several generations into the respective disease model strain.

The transgenic animals of the invention can also be used to study tissue distribution of E-selectin expression by various analytical methods including in situ histological analysis of the expression pattern of the reporter gene, and in vitro detection of the reporter gene in various tissues, tissue sections and/or cell types.

The invention further contemplates isolated cells or a cell culture derived from a transgenic animal (e.g., mouse) of the invention. The cells can be obtained directly from the animal, from a descendent animal, or can be a progeny of a primary culture of one or more cells of the animal. The isolated cell can be in the form of a single cell or cell line, or a composition of mixed cells. The cell can be obtained from an animal which is the descendant of a transgenic animal of this invention, such as by a cross with another animal having either the same or a different genetic background. Thus an isolated cell can be either homozygous or heterozygous for a reporter gene in the E-selectin allele. The isolated cell is preferably an endothelial cell.

In accordance with the foregoing the present invention thus provides (1) A transgenic or somatic recombinant non-human animal, e.g., a mammal, e.g., a pig, a primate, such as a monkey, or a rodent, such as a mouse or a rat, wherein expression of an exogenous soluble marker, e.g., human growth hormone or a modified, secreted heat stable alkaline phosphatase, specifically by endothelial cells, e.g., vascular endothelial cells, is regulatable by a chemical stimulus, including a cytokine, or a physical stimulus including light or temperature, e.g., a transgenic non-human animal comprising a polynucleotide encoding a soluble marker protein functionally linked to a regulatory sequence of an endogenous gene encoding E-selectin; and isolated cells of said animal.

(2) A transgenic non-human animal wherein in the presence of a stimulus, e.g., an inflammatory cytokine, a soluble marker is specifically produced by endothelial cells.

(3) A transgenic non-human animal comprising a recombinant DNA construct comprising a polynucleotide having a nucleotide sequence as illustrated in SEQ ID NO:11 or SEQ ID NO:12.

(4) A non-human animal being an offspring of a transgenic non-human animal as under (1), (2) or (3) crossed with a non-human animal showing a disease condition and/or its sequellae, e.g., symptoms, resulting from an altered genetic background, either spontaneously developed or following genetic manipulation.

(5) A transgenic non-human animal cell comprising a recombinant DNA construct comprising a polynucleotide having a nucleotide sequence as illustrated in SEQ ID NO:11 or SEQ ID NO:12.

(6) A recombinant DNA construct comprising a polynucleotide having a nucleotide sequence as illustrated in SEQ ID NO:9 or SEQ ID NO:10.

(7) A method for testing a potential therapeutic agent for a specified condition, in particular a disorder associated with inflammatory, thrombotic, ischaemic or neoplastic conditions or transplant rejection, wherein the agent is administered to a transgenic non-human animal as under (1), (2) or (3), monitoring marker concentration in a body fluid, e.g., plasma, and comparing the result with the result obtained from an untreated transgenic or somatic recombinant non-human animal as under (1), (2) or (3), an elevated level being indicative of the potential of the agent.

(8) A method for screening of modulators of E-selectin expression comprising the steps of
  (a) administering the potential modulator to a transgenic or somatic recombinant non-human animal as under (1), (2) or (3),
  (b) monitoring marker concentration in a body fluid, e.g., plasma, and
  (c) comparing the result with the result obtained from an untreated transgenic or somatic recombinant non-human animal as under (1), (2) or (3), a modulated level being indicative of the therapeutic potential of the agent.

(9) A novel modulator of E-selectin expression identified by a method as under (6) or (7).

(10) A method for treating a patient suffering from an inflammatory, thrombotic, ischaemic or neoplastic condition or from transplant rejection comprising administering to the patient a pharmaceutically effective amount of a modulator as under (8).

(11) A method to monitor disease development and progression in established models of disease involving spontanously developing or induced disease conditions in wild-type or transgenic animals comprising
  (a) crossing of the transgenic non-human animals as under (1), (2) or (3) with animal strains known for their use as animal models and
  (b) monitoring disease progression in offsprings in relation to marker concentration in a body fluid.

The following examples illustrate the invention without limitation.

EXAMPLE 1

Preparation of Transgenic Mice Expressing a Secreted Heat Stable Alkaline Phosphatase Gene Under the Control of the E-selectin Regulatory Sequence Without the 3'UTR of E-selectin Containing the mRNA Destabilizing AUUUA Repeats (a) Preparation of DNA Construct (i) Mutation of the ATG Start Codon The ATG start site of E-selectin is mutated from . . . GTC ATG AAT . . . to . . . GTC AAT TG AAT . . . to introduce a unique Mfe I restriction site (underlined) within the genomic E-selectin fragment for cloning of SEAP, as follows:

A ~6 kb XbaI genomic mouse E-selectin clone (D3-ES cells) in the pBS-KS(-) vector (Stratagene) is used to modify the ATG start codon by PCR. The 5'-fragment is amplified by PCR using the primerpair SEQ ID NO:1 and SEQ ID NO:2 [50 µl standard reactions are prepared using 400 nM primer, 200 nM dNTP's, PCR buffer with 1.5 mM $MgCl_2$, 1.5 U Taq DNA polymerase in a PTC-200 thermocycler].

The 3'-fragment is amplified with the primerpair SEQ ID NO:3 and SEQ ID NO:4. The two fragments are purified using agarose gel electrophoresis. 200 fmol of each partial fragment is used for a PCR pre-amplification without primers to generate the full-length fragment (4×94° 60"; 40° 120"; 72° 120"). The full-length fragment is amplified using primers SEQ ID NO:1 and SEQ ID NO:2 in a standard PCR reaction. The PCR fragment is gel purified, digested with Afl-2, the DNA precipitated using sodium acetate/ethanol, cut with BamH1 and purified by agarose electrophoresis.

(ii) mE-selectin With Mutated ATG (mE-Sel/mutATG).

Genomic Xbal/mE-Sel/pBS-KS(-) clone (is partially cut with BamH1, the 8.5 kb fragment isolated using gel electrophoresis and digested with Afl-2. The 8 kb fragment is purified and ligated with the 520 bp PCR fragment obtained in (i) above carrying the mutated ATG start codon. The ligation mixture is precipitated (sodium acetate/ethanol) and redissolved in TE Buffer pH 8.0. 2 μg (20%) of the ligation is electroporated into *E.coli* XL1-blue electrocompetent cells and clones screened by PCR followed by precipitation and digestion. Several positive clones are verified by sequencing using standard protocol.

(iii) mE-selectin with Mutated ATG/Neo Cassette (mE-Sel/mutATG/Neo).

2.3 μg plasmid mE-Sel/mutATG is linearised with Afl-2 and blunt ended with Klenow DNA polymerase using standard protocol and the gel purified vector is dephosphorylated with Shrimp alkaline phosphatase (SAP). The Neo cassette is isolated by digesting 5 μg plasmid pRay-2 [Storck et al., Nucleic Acids Res. 24:4594–4596 (1996)] with Xho-1, the DNA precipitated cut with Xma-1. The 1400 bp NeoloxP fragment is purified by gel electrophoresis and 0.5 μg of the isolated fragment is blunt ended using Klenow. 7 fmol Vector and 20 fmol NeoloxP fragment are ligated und electroporated into *E.coli* XL1-blue, clones selected by PCR (SEQ ID NO:1 and SEQ ID NO:2). Several isolated plasmids are controlled by restriction digest (Sph1, Xba1, Nco1, BamH1) and for a 3'–5' orientation of the NeoloxP insert.

(iv) mE-Selectin with SEAP-2 in Mutated ATG Site (mE-Sel/SEAP-2/Neo).

5 μg plasmid mE-Sel/mutATG/Neo is linearized with Mfe-1, purified by gel electrophoresis and the isolated vector dephosphorylated with SAP. The SEAP-2 fragment is isolated from 5 μg plasmid "pSEAP2" (Accession No: U09660; Clontech) by EcoR1 and Mfe-1 digestion. The 1703 bp fragment is purified using gel electrophoresis. 5 fmol vector and 20 fmol SEAP-2 are ligated and electroporated into *E.coli* XL1-blue as described above. Clones are selected by plasmid digestion using Nde-1; BamH1; Xba-1 and the sequence of several positive clones is verified by DNA sequencing. FIG. 1 schematically depicts the insertion of the SEAP-2 fragment into linearized mE-Sel/mutATG/Neo.

v) Generation of Targeting Construct SEQ ID NO:9.

6.6 μg plasmid mE-Sel/SEAP-2/Neo is linearized with Bpu101 and the 6370 bp fragment isolated by gel electrophoresis and blunt ended with Klenow. 2 μg plasmid pBS2-SK(-) (Stratagene) is linearised with EcoRV, purified and dephosphorylated with SAP. 30 fmol Bpu10l fragment are ligated with 15 fmol vector pBS2SK and electroporated into *E.coli* XL1-blue. Clones are selected by Xba-1, BamH1, and EcoR1 digestion. 120 μg endotoxin-free plasmid Tar-mE-Sel SEAP-2/Neo is linearised with Not-1, heat inactivated, precipitated and redissolved in 70 μl TE Buffer low EDTA (0.1 mmolar). The resulting targeting construct is a polynucleotide having SEQ. ID. NO:9. FIG. 2(*a*) depicts the SEAP-2 targeting construct and its insertion site in the endogenous E-selectin locus.

(b) Generation of E-selectin-SEAP Knock-in BALB/c ES Cell Lines.

5×10⁶ BALB/c ES cells [Noben-Trauth et al., Transgenic Res. 5:487–491 (1996)] are electroporated with 30 μg of the linearized targeting construct. Transfected cells are selected with G418 (200 μg/ml). FIG. 2(*b*) schematically depicts the targeting construct as inserted into the targeted locus of the endogenous E-selectin gene. G418-resistant clones are screened for homologous recombination events by PCR [the ES cells are lysed 1 h/37° with 20 μl Lysis buffer (PCR buffer 1×; SDS 1.7 μM; Proteinase K 50 μg/ml) heat inactivated 85°/15 Min. and cleared by centrifugation. 1,3 μl lysed solution is used in for a 50 μl nested PCR. PCR (1): primer pair SEQ ID NO:5 and SEQ ID NO:6 (20 cycles) followed by PCR (2): 1.3 ul PCR (1) and primer pair SEQ ID NO:7 and SEQ ID NO:8 using 25 cycles.] and positive clones are further verified by Southern analysis.

Targeted ES lines are subjected to a further electroporation with a plasmid carrying the Cre gene under the transcriptional control of the HSV tk-promoter. Individual clones are grown in duplicate 96-well plates in the presence or absence of G418. The targeted locus after Cre-mediated neo cassette removal (leaving one loxP locus) is depicted in FIG. 2(*c*). The absence of the neo selection cassette is verified by Southern blot analysis of individual G418 sensitive clones.

(c) Generation of E-selectin-SEAP Knock-in Mice

BALB/c-ES cell clones carrying one E-selectin-SEAP allele are injected into BL/6-III host blastocysts and transferred into pseudopregnant foster mothers according to standard protocols. Chimeras are mated with BALB/c females and albino offspring (indicative for germ line transmission) are analyzed by PCR for target integration [200 ng genomic DNA are used in the same nested PCR as described in (vi) but in 30 μl reactions] and Southern analysis. Heterozygous animals are generated by back-crossing of F1 animals to Balb/c wild type animals and Southern analysis of the F2 animals. The homozygous lines are established by mating heterozygous F1 animals.

EXAMPLE 2

Preparation of Transgenic Mice Expressing a Secreted Heat Stable Alkaline Phosphatase Gene Under the Control of an E-selectin Regulatory Sequence Maintaining the 3'UTR of E-selectin Containing the mRNA Destabilizing AUUUA Repeats (a) Preparation of DNA Construct.

(i) mE-Selectin with SEAP-1 in Mutated ATG Site (mE-Sel/SEAP-1/Neo).

5 μg plasmid obtained in Example 1(a)(ii) is cut with EcoR1 and Bsm-1 and the 1615 bp fragment purified by gel electrophoresis. 45 fmol SEAP-1 fragment is ligated into 5 fmol mE-Sel/mutATG/Neo, linearized with Mfe-1 and dephosphorylated, using 22 fmol Linker Bsm-1/Mfe-1 (GTTTAA). FIG. 1 schematically depicts the insertion of the SEAP-1 fragment into linearized mE-Sel/mutATG/Neo. Clone selection and sequencing are done as described above. The selected clone has a deletion of two base pairs (CA) in the Bsm1 site located 40 bp 3' of the Stop codon.

(ii) Generation of Targeting Construct SEQ ID NO:10.

5 μg plasmid mE-Sel/SEAP-1/Neo are treated as described above. 120 μg endotoxin-free plasmid Tar-mE-Sel SEAP-1/Neo is linearised with Not-1, heat inactivated, precipitated and redissolved in TE buffer (0.1 mM EDTA). The resulting targeting construct is a polynucleotide having SEQ. ID. NO:10. FIG. 2(*a*) depicts the SEAP-1 targeting construct and its insertion site in the endogenous E-selectin locus.

(b) Generation of E-selectin-SEAP Knock-in BALB/c ES Cell Lines and Mice.

Cell lines and mice are generated following the protocol as described in Example 1 (b) and (c) above.

Test 1: LPS and Cytokine Induction of SEAP Expression in Heterozygous Mice.

Heterozygous mice of Example 1 and Example 2 are injected with LPS (Sigma, Serotype 0:111B4 Cat. L4130) at a dose of 25 µg per mouse. Murine recombinant TNFα (R&D Systems, Cat No. 410-MT) is diluted in sterile saline and administered at a dose of 500 ng/mouse. Administration is intravenously, e.g., into the tail vein, subcutaneously or intraperitoneally.

Blood for analysis is taken from a superficial vein of the mouse into heparinized glass hematocrit capillaries. The blood is centrifuged in a table-top Eppendorff centrifuge at maximal speed for 5 min to prepare plasma.

A standard curve is created with human placental alkaline phosphatase (PAP) (Sigma Cat. P-3895). A stock solution of 2 mg/ml dissolved in buffer (Tris/HCl 50 mM pH 7.4; NaCl 150 mM; BSA 1%) is stored at −80° C. in aliquots. The standard curve is diluted in mouse plasma containing Heparin. The range of the standard curve is between 0.5 and 50000 ng/mL PAP.

For the enzyme assay the Tropix Kit (Tropix, Cat. No BP300) is used. The analysis of heat stable alkaline phosphatase activity in standards and samples is performed in duplicates according to the manufacturer's suggestion.

Figure 3:
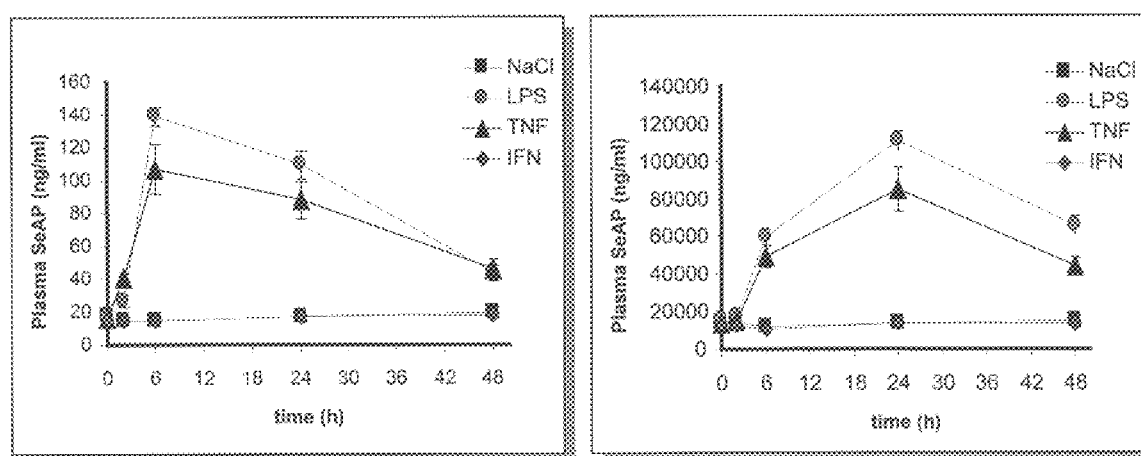
FIG. 3 ("Induction of SEAP by cytokines or LPS") depicts elevated plasma levels of SEAP-1 (left panel) or SEAP-2 (right panel) in TNF- or LPS-induced heterozygous lines, with maximum levels of plama SEAP attained at 6 hours (SEAP-1) or 24 hours (SEAP-2) post-stimulation; and by comparison the absence of induction in NaCl or IFN controls.
Figure 4:
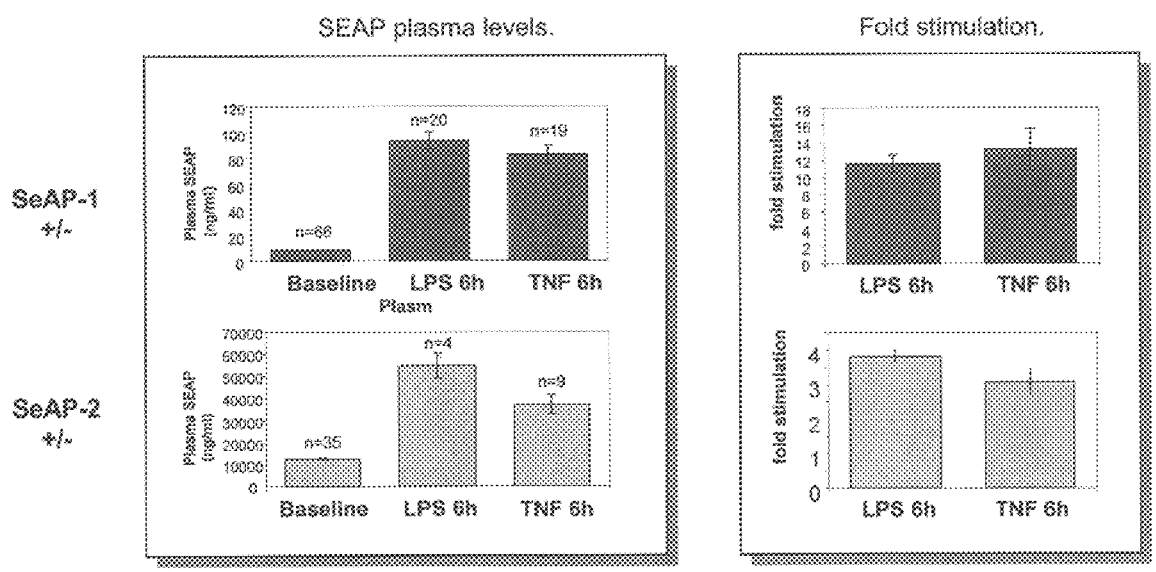
FIG. 4 ("Analysis of SEAP expression in the two lines") is a bar chart representing pooled data from n experiments which shows elevated plasma levels of SEAP-1- and SEAP-2 (left panel) and fold stimulation (right panel) in transgenic heterozygous (+/−) mice at 6 hours following LPS or TNF induction, compared to baseline levels.

The results are plotted in FIGS. 3 and 4. FIG. 3 shows that animals of Example 1 and Example 2 display significantly increased levels of circulating SEAP 6 hours after the administration of LPS as well as TNFα. The maximal levels of plasma SEAP are reached at 6 hours post-stimulation in animals of Example 2, the maximum reached in animals of Example 1 is not seen until 24 hours post stimulation. SEAP-2 mice express about 1000-fold more marker enzyme than SEAourP-1 animals. NaCl and IFNg (which are known not to induce E-selectin in vitro) have no effect on SEAP induction in either line, demonstrating that SEAP expression follows the same stimulation pattern as E-selectin. FIG. 4 shows pooled data obtained at the 6 hour time point from n experiments. The plasma levels and the stimulation factors are shown (means+/−SEM). In the SEAP-1 line, LPS- or TNF-stimulated SEAP expression at 6 hours is higher than in the SEAP-2 line (about 10-fold vs. about 3-fold).

Test 2: LPS and Cytokine Induction of SEAP Expression in Homozygous Mice.

Figure 5:
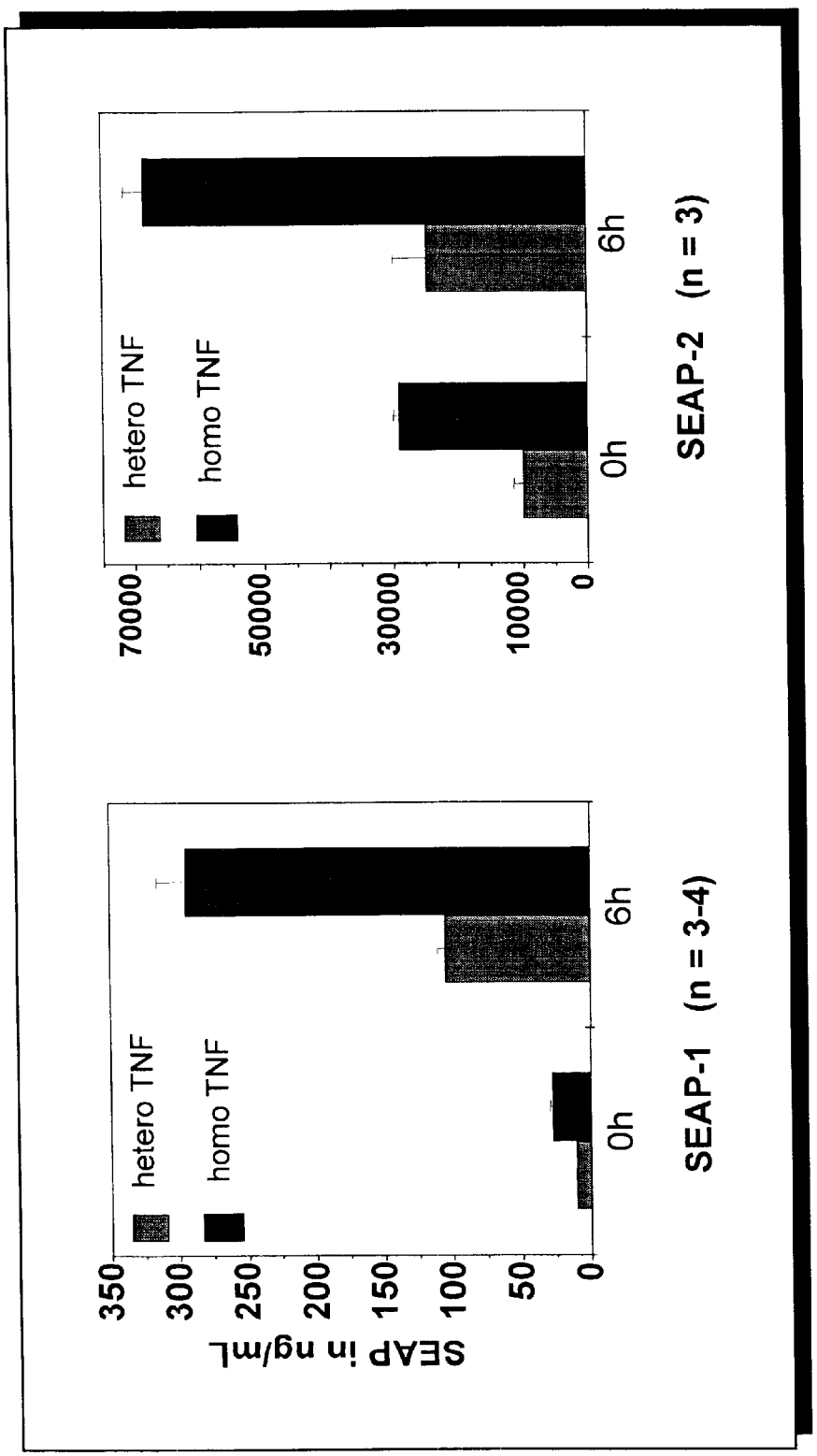
FIG. 5 ("Comparison of heterozygous and homozygous animals.") is a bar chart representing pooled data from n experiments which shows elevated plasma levels of SEAP-1 (left panel) and SEAP-2 (right panel) in transgenic homozygous TNF-induced lines relative to transgenic heterozygous lines.

The baseline plasma levels of SEAP is consistently and significantly higher in the homozygous compared to the heterozygous animals. The level of expression 6 hours after TNFα challenge is about 3-fold higher in the homozygous mice compared to the heterozygous animals of Example 1 and Example 2 while no change is seen in either line in saline-injected control animals. FIG. 5 depicts a comparison of blood samples taken from heterozygous and homozygous mice treated with murine TNFa (500 ng/mouse) at 6 hours after stimulation (means+/−SEM of n animals per group).

Test 3: Analysis of the Site of SEAP Expression.

Animals from Example 1 and Example 2 are treated with either LPS or saline, killed after 6 hours and organs removed for histology. Wild-type animals serve as controls.

After fixation for 3 hours in 4% PBS-buffered paraformaldehyde, tissues are infused with sucrose over night, embedded in OCT compound and snap frozen. The following results are obtained with tongue tissue. Cryosections (8 µm) are taken on polylysine coated slides, briefly dried and then stored at −80° C. For enzyme histochemistry, slides are brought to room temperature and then incubated for 45 min at 65° C. in 50 mM Tris/100 mM NaCl. The sections are cooled to room temperature and further incubated in alkaline phosphatase substrate mixture prepared as follows: 100 mg nitro tetrazolium blue and 30 mg 5-bromo-4-chloro-3-indolyl phosphate are each dissolved in 5 ml N,N-dimethylformamide and then added to 90 ml 200 mM Tris buffer pH 9.2. The sections are incubated at 37° C. for 3–4 h, briefly washed, counter-stained and inspected under a microscope. Immunohistochemistry is performed with anti CD31 and anti E-selectin antibody.

In the non-heat inactivated tissue sections from mouse tongue very strong alkaline phosphatase activity is observed in several cell types. In the sections which were heat-inactivated, the background alkaline phosphatase activity is absent in the wild type control animals as well as in the SEAP-1 animals of Example 2 and, as shown in FIG. 6, in the unstimulated SEAP-2 animal of Example 1 (boxes marked "SEAP-2 control"). In the LPS-treated animal of Example 1 (FIG. 6, boxes marked "SEAP-2 LPS") a specific staining is seen in the endothelium of some but not all vessels. The stained vessels are the same as those which express E-selectin after LPS stimulation (se FIG. 6, boxes marked "LPS"). Thus heat stable alkaline phosphatase enzyme activity is detected upon LPS stimulation in SEAP-2 mice in the same vessels as those which in wild type animals express E-selectin.

Test 4: Elimination Kinetics of SEAP. The elimination kinetics of SEAP are investigated in an experiment in which wild-type mice are injected i.v. with human alkaline phosphatase, and plasma samples are analyzed. A conventional PK method is employed to analyze plasma concentration data and to estimate amount of SEAP expressed after stimulation, yielding the following data:

|  |  | TNF |  | LPS |  |
| --- | --- | --- | --- | --- | --- |
| Animal Group | Parameters | mean | SD | mean | SD |
| SeAP-1 | AUC (ng · h/mL) | 3250 | 1040 | 3990 | 660 |
|  | Expression (ng) | 321 | 102 | 393 | 65 |
| SeAP-2 | AUC (ng · h/mL) | 2740 | 700 | 3930 | 160 |
|  | Expression (? g) | 270 | 69 | 388 | 16 |

Figure 7:
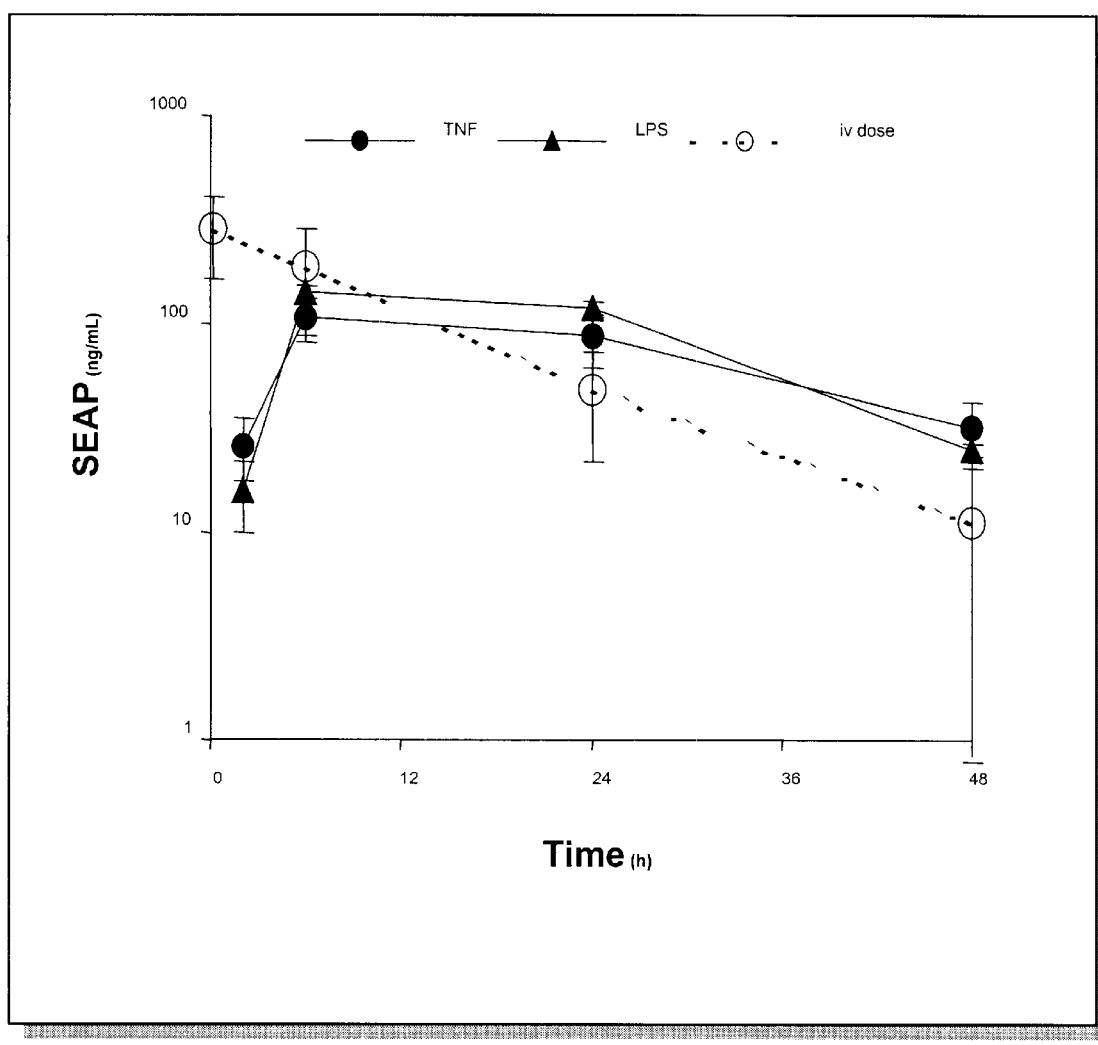
FIG. 7 charts the elimination half-life of SEAP in TNF- or LPS-treated SEAP-1 animals in relation to the elimination curve of i.v. administered alkaline phosphatase.

Endogenously produced SEAP is found to distribute mainly into the blood stream. As depicted in FIG. 7, the elimination half-life of SEAP is about 10 hours.

Test 5: Effect of Inhibitory Compounds on SEAP Expression.

Figure 8:
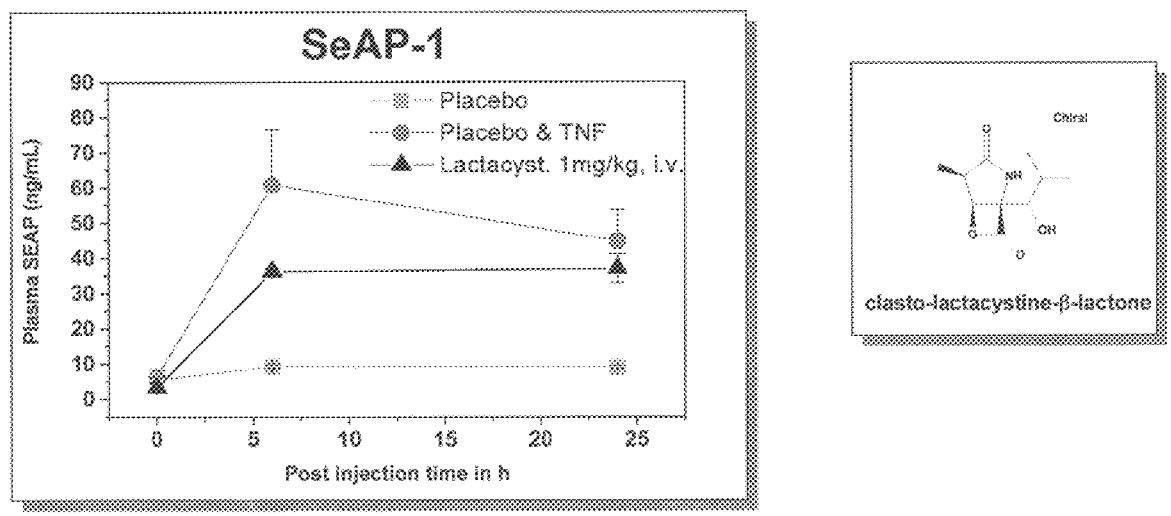
FIG. 8 ("Inhibition of SEAP expression by proteasome inhibitor.") illustrates inhibition of SEAP expression in an SEAP-1 line by a proteasome inhibitor, clastolactacystine-β-lactone, as compared to placebo, and placebo and TNF.

Clasto-lactacystine-β-lactone, a commercially available proteasome inhibitor is dissolved in DMSO (10 µl/100 µg) and further diluted with 90 µl Peg300. This mixture is further diluted 1:10 in saline and injected i.v. to animals of Example 2 at a dose of 1 mg/kg. Ten to 15 min later TNF is administered i.p. to compound-treated or untreated animals of Example 2. Blood samples are taken from the animals at baseline, 6 hours and 24 hours and SEAP levels analyzed. A significant inhibition of marker enzyme expression is observed 6 hours after TNF administration in the animals which received clasto-lactacystine-β-lactone and TNF compared to the animals which received TNF alone (p=0.045, two-way ANOVA). FIG. 8 shows that in SEAP-1 animals, the proteasome inhibitor significantly inhibits marker enzyme expression after TNF stimulation at 6 hours, but shows no effect at 24 hours in this mouse line. In SEAP-2 animals the compound does not modify SEAP expression at 6 hours or 24 hours after TNF simulation Test 6: Time Course of Endothelial Activation During Atherosclerotic Lesion Development.

Homozygous mice derived from animals from Example 1 or Example 2 are mated to homozygous mouse strains prone to atherosclerosis, e.g., LDL-R −/− or apoE −/−. The offspring of these animals are fed a high cholesterol diet. At weekly intervals blood samples are taken and marker enzyme is quantified. Mice show an increase in marker enzyme prior to fatty lesion development.

Test 7: Endothelial Cell Activation During Progression of Inflammatory Disease.

Animals from Example 1 or Example 2 are crossed with mouse strains predisposed to spontaneous development of inflammatory disorders e.g., the MRL-lpr mouse strain. Blood samples are taken from offspring at daily-to weekly time intervals and marker enzyme expression is monitored. The level of marker enzyme expression is correlated with disease onset.

What is claimed is:

1. A transgenic mouse comprising a polynucleotide encoding a soluble marker protein functionally linked to a regulatory sequence of an endogenous gene encoding E-selectin, wherein the soluble marker protein is a secreted alkaline phosphatase, and wherein the polynucleotide encoding the secreted alkaline phosphatase is inserted into a region of an E-selectin gene of a chromosomal E-selectin allele of said mouse, which is between a transcription start site and a translation start site of said E-selectin gene, and wherein said mouse expresses the secreted alkaline phosphatase by endothelial cells and said expression is regulatable by chemical stimulus or physical stimulus.

* * * * *